(12) United States Patent
Menzel et al.

(10) Patent No.: US 9,736,602 B2
(45) Date of Patent: *Aug. 15, 2017

(54) ACTUATOR SYSTEMS FOR ORAL-BASED APPLIANCES

(71) Applicant: SoundMed, LLC, Mountain View, CA (US)

(72) Inventors: Christoph Menzel, New London, NH (US); Amir A. Abolfathi, Woodside, CA (US)

(73) Assignee: SoundMed, LLC, Mountain View, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/176,617

(22) Filed: Feb. 10, 2014

(65) Prior Publication Data

US 2014/0169592 A1     Jun. 19, 2014

Related U.S. Application Data

(63) Continuation of application No. 13/615,067, filed on Sep. 13, 2012, now Pat. No. 8,649,535, which is a
(Continued)

(51) Int. Cl.
*H04R 25/00*     (2006.01)
*H04R 3/04*      (2006.01)
(Continued)

(52) U.S. Cl.
CPC ........... *H04R 25/606* (2013.01); *A61C 5/00* (2013.01); *A61C 8/0098* (2013.01); *H04R 1/46* (2013.01);
(Continued)

(58) Field of Classification Search
None
See application file for complete search history.

(56) References Cited

U.S. PATENT DOCUMENTS 2,045,404 A    6/1936  Nicholides
2,161,169 A    6/1939  Jefferis
(Continued)

FOREIGN PATENT DOCUMENTS

CN    1425264       6/2003
EP    0715838 A2    6/1996
(Continued)

OTHER PUBLICATIONS

Altmann, et al. Foresighting the new technology waves—Exper Group. In: State of the Art Reviews and Related Papers—Center on Nanotechnology and Society. 2004 Conference. Published Jun. 14, 2004. p. 1-291. Available at http://www.nano-and-society.org/NELSI/documents/ECreviewsandpapers061404.pdf. Accessed Jan. 11, 2009.
(Continued)

*Primary Examiner* — Curtis Kuntz
*Assistant Examiner* — Qin Zhu
(74) *Attorney, Agent, or Firm* — Levine Bagade Han LLP

(57) ABSTRACT

Actuator systems for oral-based appliances utilizing transducers which are attached, adhered, or otherwise embedded into or upon a dental or oral appliance to form a hearing aid assembly. Such oral appliances may be a custom-made device which receives incoming sounds and transmits the processed sounds via a vibrating transducer element. The transducer element may utilize electromagnetic or piezoelectric transducer mechanisms and may be positioned directly along the dentition or along an oral appliance housing in various configurations.

27 Claims, 32 Drawing Sheets

Related U.S. Application Data continuation of application No. 12/646,789, filed on Dec. 23, 2009, now Pat. No. 8,358,792, which is a continuation of application No. 11/741,648, filed on Apr. 27, 2007, now Pat. No. 7,724,911.

(60) Provisional application No. 60/809,244, filed on May 30, 2006, provisional application No. 60/820,223, filed on Jul. 24, 2006.

(51) Int. Cl.
    *H04R 1/46*     (2006.01)
    *A61C 5/00*     (2017.01)
    *A61C 8/00*     (2006.01)
    *B33Y 70/00*     (2015.01)
    *B33Y 80/00*     (2015.01)

(52) U.S. Cl.
CPC ............. *H04R 3/04* (2013.01); *H04R 25/602* (2013.01); *B33Y 70/00* (2014.12); *B33Y 80/00* (2014.12); *H04R 25/604* (2013.01); *H04R 2225/31* (2013.01); *H04R 2225/67* (2013.01); *H04R 2420/07* (2013.01); *H04R 2460/01* (2013.01); *H04R 2460/13* (2013.01)

(56) References Cited

U.S. PATENT DOCUMENTS

| | | |
|---|---|---|
| 2,230,397 A | 2/1941 | Abraham |
| 2,242,118 A | 5/1941 | Fischer |
| 2,318,872 A | 5/1943 | Madiera |
| 2,977,425 A | 3/1961 | Cole |
| 2,995,633 A | 8/1961 | Puharich et al. |
| 3,156,787 A | 11/1964 | Puharich et al. |
| 3,170,993 A | 2/1965 | Puharich et al. |
| 3,267,931 A | 8/1966 | Puharich et al. |
| 3,325,743 A | 6/1967 | Blum |
| 3,712,962 A | 1/1973 | Epley |
| 3,787,641 A | 1/1974 | Santori |
| 3,894,196 A | 7/1975 | Briskey |
| 3,985,977 A | 10/1976 | Beaty et al. |
| 4,025,732 A | 5/1977 | Traunmuller |
| 4,150,262 A | 4/1979 | Ono |
| 4,498,461 A | 2/1985 | Hakansson |
| 4,591,668 A | 5/1986 | Iwata |
| 4,612,915 A | 9/1986 | Hough et al. |
| 4,642,769 A | 2/1987 | Petrofsky |
| 4,738,268 A | 4/1988 | Kipnis |
| 4,791,673 A | 12/1988 | Schreiber |
| 4,817,044 A | 3/1989 | Ogren |
| 4,832,033 A | 5/1989 | Maher et al. |
| 4,904,233 A | 2/1990 | Haakansson et al. |
| 4,920,984 A | 5/1990 | Furumichi et al. |
| 4,962,559 A | 10/1990 | Schuman |
| 4,982,434 A | 1/1991 | Lenhardt et al. |
| 5,012,520 A | 4/1991 | Steeger |
| 5,033,999 A | 7/1991 | Mersky |
| 5,047,994 A | 9/1991 | Lenhardt et al. |
| 5,060,526 A | 10/1991 | Barth et al. |
| 5,082,007 A | 1/1992 | Adell |
| 5,233,987 A | 8/1993 | Fabian et al. |
| 5,323,468 A | 6/1994 | Bottesch |
| 5,325,436 A | 6/1994 | Soli et al. |
| 5,354,326 A | 10/1994 | Comben et al. |
| 5,372,142 A | 12/1994 | Madsen et al. |
| 5,402,496 A | 3/1995 | Soli et al. |
| 5,403,262 A | 4/1995 | Gooch |
| 5,447,489 A | 9/1995 | Issalene et al. |
| 5,455,842 A | 10/1995 | Merskey et al. |
| 5,460,593 A | 10/1995 | Mersky et al. |
| 5,477,489 A | 12/1995 | Wiedmann |
| 5,546,459 A | 8/1996 | Sih et al. |
| 5,558,618 A | 9/1996 | Maniglia |
| 5,565,759 A | 10/1996 | Dunstan |
| 5,579,284 A | 11/1996 | May |
| 5,616,027 A | 4/1997 | Jacobs et al. |
| 5,624,376 A | 4/1997 | Ball et al. |
| 5,661,813 A | 8/1997 | Shimauchi et al. |
| 5,706,251 A | 1/1998 | May |
| 5,760,692 A | 6/1998 | Block |
| 5,793,875 A | 8/1998 | Lehr et al. |
| 5,800,336 A | 9/1998 | Ball et al. |
| 5,812,496 A | 9/1998 | Peck |
| 5,828,765 A | 10/1998 | Gable |
| 5,902,167 A | 5/1999 | Filo et al. |
| 5,914,701 A | 6/1999 | Gersheneld et al. |
| 5,961,443 A | 10/1999 | Rastatter et al. |
| 5,984,681 A | 11/1999 | Huang |
| 6,029,558 A | 2/2000 | Stevens et al. |
| 6,047,074 A | 4/2000 | Zoels et al. |
| 6,057,668 A | 5/2000 | Chao |
| 6,068,590 A | 5/2000 | Brisken |
| 6,072,884 A | 6/2000 | Kates |
| 6,072,885 A | 6/2000 | Stockham, Jr. et al. |
| 6,075,557 A | 6/2000 | Holliman et al. |
| 6,115,477 A | 9/2000 | Filo et al. |
| 6,118,882 A | 9/2000 | Haynes |
| 6,171,229 B1 | 1/2001 | Kroll et al. |
| 6,223,018 B1 | 4/2001 | Fukumoto et al. |
| 6,239,705 B1 | 5/2001 | Glen |
| 6,333,269 B2 | 12/2001 | Naito et al. |
| 6,371,758 B1 | 4/2002 | Kittelsen |
| 6,377,693 B1 | 4/2002 | Lippa et al. |
| 6,394,969 B1 | 5/2002 | Lenhardt |
| 6,504,942 B1 | 1/2003 | Hong et al. |
| 6,533,747 B1 | 3/2003 | Polaschegg et al. |
| 6,538,558 B2 | 3/2003 | Sakazume et al. |
| 6,585,637 B2 | 7/2003 | Brillhart et al. |
| 6,629,922 B1 | 10/2003 | Puria et al. |
| 6,631,197 B1 | 10/2003 | Taenzer |
| 6,633,747 B1 | 10/2003 | Reiss |
| 6,658,124 B1 | 12/2003 | Meadows |
| 6,682,472 B1 | 1/2004 | Davis |
| 6,694,035 B1 | 2/2004 | Teicher et al. |
| 6,754,472 B1 | 6/2004 | Williams et al. |
| 6,778,674 B1 | 8/2004 | Panasik et al. |
| 6,826,284 B1 | 11/2004 | Benesty et al. |
| 6,885,753 B2 | 4/2005 | Bank |
| 6,917,688 B2 | 7/2005 | Yu et al. |
| 6,941,952 B1 | 9/2005 | Rush, III |
| 6,954,668 B1 | 10/2005 | Cuozzo |
| 6,985,599 B2 | 1/2006 | Asnes |
| 7,003,099 B1 | 2/2006 | Zhang et al. |
| 7,010,139 B1 | 3/2006 | Smeehuyzen |
| 7,033,313 B2 | 4/2006 | Lupin et al. |
| 7,035,415 B2 | 4/2006 | Belt et al. |
| 7,074,222 B2 | 7/2006 | Westerkull |
| 7,076,077 B2 | 7/2006 | Atsumi et al. |
| 7,099,822 B2 | 8/2006 | Zangi |
| 7,162,420 B2 | 1/2007 | Zangi et al. |
| 7,171,003 B1 | 1/2007 | Venkatesh et al. |
| 7,171,008 B2 | 1/2007 | Elko |
| 7,174,022 B1 | 2/2007 | Zhang et al. |
| 7,174,026 B2 | 2/2007 | Niederdränk |
| 7,206,423 B1 | 4/2007 | Feng et al. |
| 7,246,058 B2 | 7/2007 | Burnett |
| 7,258,533 B2 | 8/2007 | Tanner et al. |
| 7,269,266 B2 * | 9/2007 | Anjanappa ............ H04R 17/02 381/151 |
| 7,271,569 B2 | 9/2007 | Oglesbee |
| 7,281,924 B2 | 10/2007 | Ellison |
| 7,310,427 B2 | 12/2007 | Retchin et al. |
| 7,329,226 B1 | 2/2008 | Ni et al. |
| 7,331,349 B2 | 2/2008 | Brady et al. |
| 7,333,624 B2 | 2/2008 | Husung |
| 7,361,216 B2 | 4/2008 | Kangas et al. |
| 7,409,070 B2 | 8/2008 | Pitulia |
| 7,486,798 B2 | 2/2009 | Anjanappa et al. |
| 7,512,448 B2 | 3/2009 | Malick et al. |
| 7,520,851 B2 | 4/2009 | Davis et al. |
| 7,522,738 B2 | 4/2009 | Miller, III |
| 7,522,740 B2 | 4/2009 | Julstrom et al. |
| 7,664,277 B2 | 2/2010 | Abolfathi et al. |

(56) References Cited

U.S. PATENT DOCUMENTS

| | | |
|---|---|---|
| 7,680,284 B2 | 3/2010 | Lee et al. |
| 7,724,911 B2 | 5/2010 | Menzel et al. |
| 7,796,769 B2 | 9/2010 | Abolfathi |
| 7,801,319 B2 | 9/2010 | Abolfathi |
| 7,844,064 B2 | 11/2010 | Abolfathi et al. |
| 7,844,070 B2 | 11/2010 | Abolfathi |
| 7,876,906 B2 | 1/2011 | Abolfathi |
| 8,189,838 B1 | 5/2012 | Rich |
| 8,254,611 B2 | 8/2012 | Abolfathi et al. |
| 8,270,638 B2 | 9/2012 | Abolfathi et al. |
| 8,588,447 B2 | 11/2013 | Abolfathi et al. |
| 2001/0003788 A1 | 6/2001 | Ball et al. |
| 2001/0051776 A1 | 12/2001 | Lenhardt |
| 2002/0026091 A1 | 2/2002 | Leysieffer |
| 2002/0039427 A1* | 4/2002 | Whitwell et al. ............ 381/312 |
| 2002/0071581 A1 | 6/2002 | Leysieffer et al. |
| 2002/0077831 A1 | 6/2002 | Numa |
| 2002/0122563 A1 | 9/2002 | Schumaier |
| 2002/0173697 A1 | 11/2002 | Lenhardt |
| 2003/0048915 A1 | 3/2003 | Bank |
| 2003/0059078 A1 | 3/2003 | Downs et al. |
| 2003/0091200 A1 | 5/2003 | Pompei |
| 2003/0212319 A1 | 11/2003 | Magill |
| 2004/0057591 A1 | 3/2004 | Beck et al. |
| 2004/0063073 A1 | 4/2004 | Kajimoto et al. |
| 2004/0131200 A1 | 7/2004 | Davis |
| 2004/0141624 A1 | 7/2004 | Davis et al. |
| 2004/0202339 A1 | 10/2004 | O'Brien, Jr. et al. |
| 2004/0202344 A1 | 10/2004 | Anjanappa et al. |
| 2004/0214130 A1 | 10/2004 | Fischer et al. |
| 2004/0243481 A1 | 12/2004 | Bradbury et al. |
| 2004/0247143 A1 | 12/2004 | Lantrua et al. |
| 2005/0037312 A1 | 2/2005 | Uchida |
| 2005/0067816 A1 | 3/2005 | Buckman |
| 2005/0070782 A1 | 3/2005 | Brodkin |
| 2005/0129257 A1 | 6/2005 | Tamura |
| 2005/0189910 A1 | 9/2005 | Hui |
| 2005/0196008 A1 | 9/2005 | Anjanappa et al. |
| 2005/0241646 A1 | 11/2005 | Sotos et al. |
| 2006/0008106 A1 | 1/2006 | Harper |
| 2006/0025648 A1 | 2/2006 | Lupin et al. |
| 2006/0064037 A1 | 3/2006 | Shalon et al. |
| 2006/0167335 A1 | 7/2006 | Park et al. |
| 2006/0207611 A1 | 9/2006 | Anonsen |
| 2006/0270467 A1 | 11/2006 | Song et al. |
| 2006/0275739 A1 | 12/2006 | Ray |
| 2007/0010704 A1 | 1/2007 | Pitulia |
| 2007/0035917 A1 | 2/2007 | Hotelling et al. |
| 2007/0036370 A1 | 2/2007 | Granovetter et al. |
| 2007/0041595 A1 | 2/2007 | Carazo et al. |
| 2007/0105072 A1 | 5/2007 | Koljonen |
| 2007/0142072 A1 | 6/2007 | Lassally |
| 2007/0223735 A1 | 9/2007 | LoPresti et al. |
| 2007/0230713 A1 | 10/2007 | Davis |
| 2007/0242835 A1 | 10/2007 | Davis |
| 2007/0265533 A1 | 11/2007 | Tran |
| 2007/0276270 A1 | 11/2007 | Tran |
| 2007/0280491 A1 | 12/2007 | Abolfathi |
| 2007/0280492 A1 | 12/2007 | Abolfathi |
| 2007/0280493 A1 | 12/2007 | Abolfathi |
| 2007/0280495 A1 | 12/2007 | Abolfathi |
| 2007/0286440 A1 | 12/2007 | Abolfathi et al. |
| 2007/0291972 A1 | 12/2007 | Abolfathi et al. |
| 2008/0019542 A1 | 1/2008 | Menzel et al. |
| 2008/0019557 A1 | 1/2008 | Bevirt et al. |
| 2008/0021327 A1 | 1/2008 | El-Bialy et al. |
| 2008/0064993 A1 | 3/2008 | Abolfathi et al. |
| 2008/0070181 A1 | 3/2008 | Abolfathi et al. |
| 2008/0109972 A1 | 5/2008 | Mah et al. |
| 2008/0205678 A1 | 8/2008 | Boguslavskij et al. |
| 2008/0304677 A1 | 12/2008 | Abolfathi et al. |
| 2009/0028352 A1 | 1/2009 | Petroff |
| 2009/0052698 A1 | 2/2009 | Rader et al. |
| 2009/0088598 A1 | 4/2009 | Abolfathi |
| 2009/0097684 A1 | 4/2009 | Abolfathi et al. |
| 2009/0097685 A1 | 4/2009 | Menzel et al. |
| 2009/0099408 A1 | 4/2009 | Abolfathi et al. |
| 2009/0105523 A1 | 4/2009 | Kassayan et al. |
| 2009/0147976 A1 | 6/2009 | Abolfathi |
| 2009/0149722 A1 | 6/2009 | Abolfathi et al. |
| 2009/0180652 A1 | 7/2009 | Davis et al. |
| 2009/0220115 A1 | 9/2009 | Lantrua |
| 2009/0226020 A1 | 9/2009 | Abolfathi |
| 2010/0189288 A1 | 7/2010 | Menzel et al. |
| 2010/0220883 A1 | 9/2010 | Menzel et al. |
| 2010/0312568 A1 | 12/2010 | Abolfathi |
| 2010/0322449 A1 | 12/2010 | Abolfathi |
| 2011/0002492 A1 | 1/2011 | Abolfathi et al. |
| 2011/0026740 A1 | 2/2011 | Abolfathi |
| 2011/0116659 A1 | 5/2011 | Abolfathi |
| 2012/0321113 A1 | 12/2012 | Abolfathi |
| 2013/0010987 A1 | 1/2013 | Abolfathi et al. |

FOREIGN PATENT DOCUMENTS

| | | |
|---|---|---|
| EP | 0824889 A1 | 2/1998 |
| EP | 1783919 A1 | 5/2007 |
| GB | 1066299 A | 4/1967 |
| JP | 56-026490 | 3/1981 |
| JP | 2007028248 A2 | 2/2007 |
| JP | 2007028610 A2 | 2/2007 |
| JP | 2007044284 A2 | 2/2007 |
| JP | 2007049599 A2 | 2/2007 |
| JP | 2007049658 A2 | 2/2007 |
| WO | WO 83/02047 | 6/1983 |
| WO | WO 91/02678 | 3/1991 |
| WO | WO 95/06398 | 3/1995 |
| WO | WO 95/19678 | 7/1995 |
| WO | WO 96/21335 | 7/1996 |
| WO | WO 02/09622 | 2/2002 |
| WO | WO 03/001845 | 1/2003 |
| WO | WO 2004/045242 | 5/2004 |
| WO | WO 2004/093493 | 10/2004 |
| WO | WO 2004/105650 | 12/2004 |
| WO | WO 2005/000391 | 1/2005 |
| WO | WO 2005/037153 | 4/2005 |
| WO | WO 2005/053533 | 6/2005 |
| WO | WO 2006/044161 | 4/2006 |
| WO | WO 2006/086410 | 8/2006 |
| WO | WO 2006/130909 | 12/2006 |
| WO | WO 2007/043055 | 4/2007 |

OTHER PUBLICATIONS

Berard, G., "Hearing Equals Behavior" [summary], 1993;http://www.bixby.org/faq/tinnitus/treatment.html.

Bozkaya, D. et al., "Mechanics of the Tapered interference Fit in Dental Implants." published Oct. 2002 [online], retrieved Oct. 14, 2010. http://www1.coe.neu.edu/~smuftu/Papers/paper-interference-fit-elsevier-2.pdf.

Broyhill, D., "Battlefield Medical Information System—Telemedicine," A research paper presented to the U.S. Army Command and General Staff College in partial Fulfillment of the requirement for A462 Combat Health Support Seminar, 12 pages, 2003.

Dental Cements—Premarket Notification, U.S. Department of Health and Human Services Food and Drug Administration Center for Devices and Radiological Health, pp. 1-10, Aug. 18, 1998.

Henry, et al. "Comparison of Custom Sounds for Achieving Tinnitus Relief, " *J Am Acad Audiol*,15:585-598, 2004.

Jastreboff, Pawel, J., "Phantom auditory perception (tinnitus): mechanisms of generation and perception," *Neuroscience Research*, 221-254, 1990, Elsevier Scientific Publishers Ireland, Ltd.

Robb, "Tinnitus Device Directory Part I." *Tinnitus Today*, p. 22, Jun. 2003.

Song, S. et al., "A 0.2-mW 2-Mb/s Digital Transceiver Based on Wideband Signaling for Human Body Communications," *IEEE J Solid-State Cir*, 42(9), 2021-2033, Sep. 2007.

"Special Forces Smart Noise Cancellation Ear Buds with Built-In GPS," http://www.gizmag.com/special-forces-smart-noise-cancellation-ear-buds-with-built-in-gps/9428/, 2 pages, 2008.

(56) References Cited

OTHER PUBLICATIONS

Stuart, A., et al., "Investigations of the Impact of Altered Auditory Feedback In-The-Ear Devices on the Speech of People Who Stutter: Initial Fitting and 4-Month Follow-Up," *Int J Lang Commun Disord*, 39(1), Jan. 2004, [abstract only].

Wen, Y. et al, "Online Prediction of Battery Lifetime for Embedded and Mobile Devices," Special Issue on Embedded Systems: Springer-Verlag Heidelberg Lecture Notes in Computer Science, V3164/2004, 15 pages, Dec. 2004.

* cited by examiner

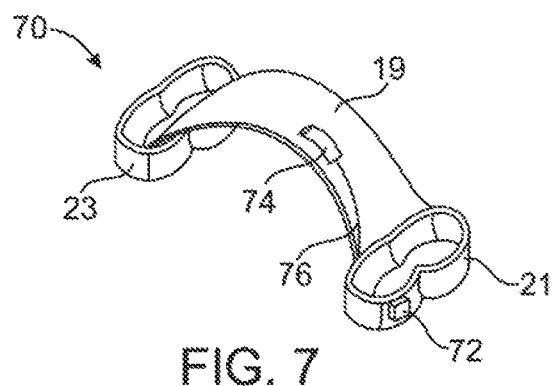
FIG. 7
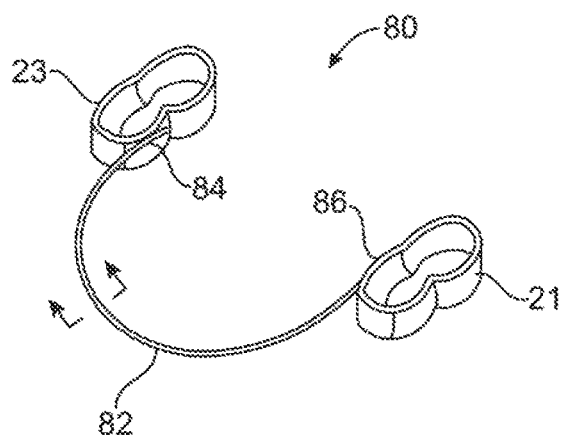
FIG. 8A
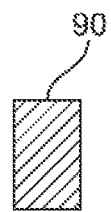        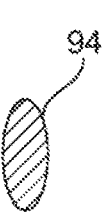    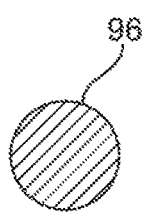
FIG. 8B    FIG. 8C    FIG. 8D    FIG. 8E

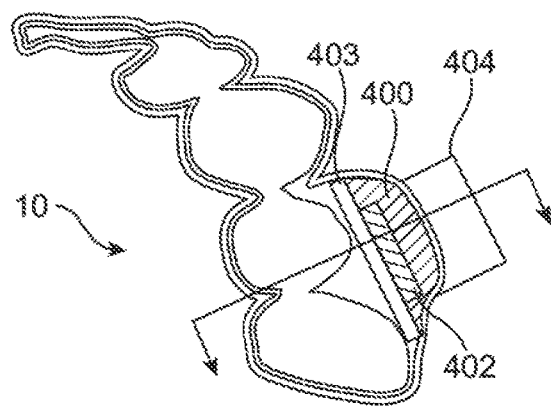
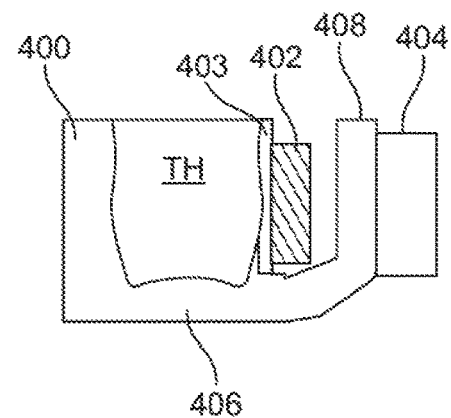
FIG. 40A  FIG. 40B
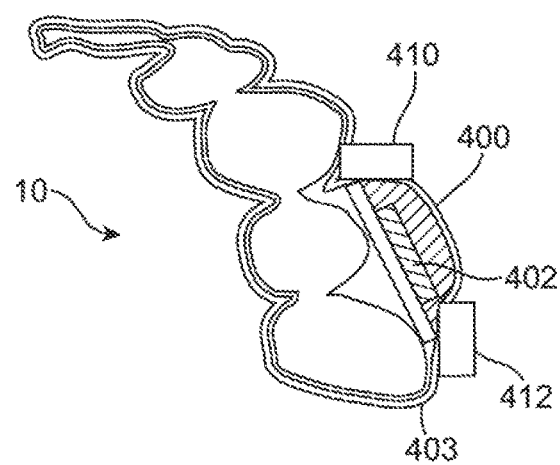
FIG. 41

ACTUATOR SYSTEMS FOR ORAL-BASED APPLIANCES

CROSS-REFERENCE TO RELATED APPLICATIONS

This application is a continuation of U.S. patent application Ser. No. 13/615,067 filed Sep. 13, 2012 (now U.S. Pat. No. 8,649,535 issued Feb. 11, 2014) which is a continuation of U.S. patent application Ser. No. 12/646,789 filed Dec. 23, 2009 (now U.S. Pat. No. 8,358,792 issued Jan. 22, 2013), which is a continuation of U.S. patent application Ser. No. 11/741,648 filed Apr. 27, 2007 (now U.S. Pat. No. 7,724,911 issued May 25, 2010), which claims the benefit of priority to U.S. Provisional Patent Application Nos. 60/809,244 filed May 30, 2006 and 60/820,223 filed Jul. 24, 2006, each of which are incorporated herein by reference in their entirety.

FIELD OF THE INVENTION

The present invention relates to methods and apparatus for conducting audio signals as vibrations through teeth or bone structures in and/or around a mouth. More particularly, the present invention relates to methods and apparatus for transmitting audio signals via sound conduction through teeth or bone structures in and/or around the mouth such that the transmitted signals correlate to auditory signals received by a user.

BACKGROUND OF THE INVENTION

Hearing loss affects over 31 million people in the United States (about 13% of the population). As a chronic condition, the incidence of hearing impairment rivals that of heart disease and, like heart disease, the incidence of hearing impairment increases sharply with age.

While the vast majority of those with hearing loss can be helped by a well-fitted, high quality hearing device, only 22% of the total hearing impaired population own hearing devices. Current products and distribution methods are not able to satisfy or reach over 20 million persons with hearing impairment in the U.S. alone.

Hearing loss adversely affects a person's quality of life and psychological well-being. Individuals with hearing impairment often withdraw from social interactions to avoid frustrations resulting fern inability to understand conversations. Recent studies have shown that hearing impairment causes increased stress levels, reduced self-confidence, reduced sociability and reduced effectiveness in the workplace.

The human ear generally comprises three regions: the outer ear, the middle ear, and the inner ear. The outer ear generally comprises the external auricle and the ear canal, which is a tubular pathway through which sound reaches the middle ear. The outer ear is separated from the middle ear by the tympanic membrane (eardrum). The middle ear generally comprises three small bones, known as the ossicles, which form a mechanical conductor from the tympanic membrane to the inner ear. Finally, the inner ear includes the cochlea, which is a fluid-filled structure that contains a large number of delicate sensory hair cells that are connected to the auditory nerve.

Hearing loss can also be classified in terms of being conductive, sensorineural or a combination of both. Conductive hearing impairment typically results from diseases or disorders that limit the transmission of sound through the middle ear. Most conductive impairments can be treated medically or surgically. Purely conductive hearing loss represents a relatively small portion of the total hearing impaired population (estimated at less than 5% of the total hearing impaired population).

Sensorineural hearing losses occur mostly in the inner ear and account for the vast majority of hearing impairment (estimated at 90-95% of the total hearing impaired population). Sensorineural hearing impairment (sometimes called "nerve loss") is largely caused by damage to the sensory hair cells inside the cochlea. Sensorineural hearing impairment occurs naturally as a result of aging or prolonged exposure to loud music and noise. This type of hearing loss cannot be reversed nor can it be medically or surgically treated; however, the use of properly fitted hearing devices can improve the individual's quality of life.

Conventional hearing devices are the most common devices used to treat mild to severe sensorineural hearing impairment. These are acoustic devices that amplify sound to the tympanic membrane. These devices are individually customizable to the patient's physical and acoustical characteristics over four to six separate visits to an audiologist or hearing instrument specialist. Such devices generally comprise a microphone, amplifier, battery, and speaker. Recently, hearing device manufacturers have increased the sophistication of sound processing, often using digital technology, to provide features such as programmability and multi-band compression. Although these devices have been miniaturized and are less obtrusive, they are still visible and have major acoustic limitation.

Industry research has shown that the primary obstacles for not purchasing a hearing device generally include: a) the stigma associated with wearing a hearing device; b) dissenting attitudes on the part of the medical profession, particularly ENT physicians; c) product value issues related to perceived performance problems; d) general lack of information and education at the consumer and physician level; and e) negative word-of-mouth from dissatisfied users.

Other devices such as cochlear implants have been developed for people who have severe to profound hearing loss and are essentially deaf (approximately 2% of the total hearing impaired population). The electrode of a cochlear implant is inserted into the inner ear in an invasive and non-reversible surgery. The electrode electrically stimulates the auditory nerve through an electrode array that provides audible cues to the user, which are not usually interpreted by the brain as normal sound. Users generally require intensive and extended counseling and training following surgery to achieve the expected benefit.

Other devices such as electronic middle ear implants generally are surgically placed within the middle ear of the hearing impaired. They are surgically implanted devices with an externally worn component.

The manufacture, fitting and dispensing of hearing devices remain an arcane and inefficient process. Most hearing devices are custom manufactured, fabricated by the manufacturer to fit the ear of each prospective purchaser. An impression of the ear canal is taken by the dispenser (either an audiologist or licensed hearing instrument specialist) and mailed to the manufacturer for interpretation and fabrication of the custom molded rigid plastic casing. Hand-wired electronics and transducers (microphone and speaker) are then placed inside the casing, and the final product is shipped back to the dispensing professional after some period of time, typically one to two weeks.

The time cycle for dispensing a hearing device, from the first diagnostic session to the final fine-tuning session, typically spans a period over several weeks, such as six to eight weeks, and involves multiple visits with the dispenser.

Accordingly, there exists a need for methods and apparatus for receiving audio signals and processing them to efficiently transmit these signals via sound conduction through teeth or bone structures in and/or around the mouth for facilitating the treatment of hearing loss in patients.

SUMMARY OF THE INVENTION

An electronic and transducer device may be attached, adhered, or otherwise embedded into or upon a removable dental or oral appliance to form an assembly which may conduct audio signals to a user via vibratory conductance through bone for utilization, e.g., as a hearing aid assembly or other audio transmission device. Such a removable oral appliance may be a custom-made device fabricated from a thermal forming process utilizing a replicate model of a dental structure obtained by conventional dental impression methods. The electronic and transducer assembly may receive incoming sounds either directly or through a receiver to process and amplify the signals and transmit the processed sounds via a vibrating transducer element coupled to a tooth or other boric structure, such as the maxillary, mandibular, or palatine bone structure.

The assembly for transmitting vibrations via at least one tooth may generally comprise a housing having a shape which is conformable to at least a portion of the at least one tooth, and an actuatable transducer disposed within or upon the housing and in vibratory communication with a surface of the at least one tooth. Moreover, the transducer itself may be a separate assembly from the electronics and may be positioned along another surface of the tooth, such as the occlusal surface, or even attached to an implanted post or screw embedded into the underlying bone.

The transducer utilized in the actuator assembly may be an electromagnetic transducer or a piezoelectric transducer. Piezoelectric transducers in particular may be used in various configurations due in part to the various vibrational modes which may be utilized to transmit the acoustic signals as vibrations through a tooth or teeth. Any number of transducers may be utilized for particular applications. For instance, low voltage multi-layer piezoelectric transducers manufactured by Morgan Electro Ceramics Ltd. (Wrexham, England) may be utilized for the applications described herein.

In transmitting the vibrational energy from the transducer to the user, the actuator assembly may be positioned against the tooth or teeth with an impedance matching layer placed therebetween. The impedance matching layer may be utilized to improve coupling and optimize the transmission of vibrational energy from the actuator into the tooth and to optimize the transmission into the tooth of any reflected vibrations.

One variation of the actuator assembly utilizes a mass coupled to a piezoelectric transducer. Upon application of an electric field, the induced dipole in the piezoelectric material may align to impart an oscillatory motion upon the mass. The actuator assembly may be coupled to the assembly enclosure via a single anchoring point or a symmetric anchoring feature. The mass may be attached to the composite transducer such that when the one or more transducers are activated to oscillate, a vibrational motion may be imparted to the mass via the anchor such that the resulting reaction force is sufficiently transmitted to the underlying tooth or teeth.

In yet another variation, an actuator assembly may utilize a symmetric (e.g., circularly symmetric) bender transducer assembly having one or more transducers attached to one another. The one or more transducers may be the same diameter or a second transducer may have a diameter which is less than a diameter of the first transducer. Another variation may utilize a piezoelectric cap-based design. Such a variation may utilize a piezoelectric transducer having a thickness and which is configured to oscillate in an elongational mode such that the cap may be forced to flex in a direction transverse to the elongational direction, thereby creating the reaction force for transmission into the user's tooth or teeth.

Another variation of an actuator assembly utilizing the force between a magnet contained within the assembly housing and an applied current to control the movement of a mass that may have a permanent magnet suspended via one or more flexible support members or tethers held in proximity to one or more coils. Coils may be held adjacent to the magnet via one or more relatively rigid support members and they may carry a current which is correlated to the desired auditory signals. When a current is passed through the coils in the presence of a magnetic field generated by magnet, the magnet may vibrate accordingly while suspended by support members to impart the vibrational reaction force to the tooth.

The span member of the housing assembly is desirably stiff to function as a platform which allows the transducer assembly to generate a sufficient amount of force for transmission into the tooth or teeth. Moreover, to maintain a constant level of output force generated by the transducer assembly, resonance values of the housing and transducer assemblies may be designed such that they occur outside a desirable frequency range of interest, e.g., 250 Hz to 10,000 Hz, by optimizing parameters of the housing, such as a thickness of the span member, to alter a resonant frequency of the system. Alternatively, it may be desirable to place the resonance within the region of interest to more efficiently drive the tooth.

Turning now to placement of the transducer assembly relative to the tooth or teeth and also with respect to the housing, any number of configurations is available for use. Generally, the housing may be comprised of a single continuous mechanical member configured to have portions of itself face opposite sides of the tooth or teeth. The actuator assembly may be effectively pressed against the tooth utilizing the housing as a foundation and the housing itself may be symmetric or non-uniform in its configuration. With the transducer positioned within the housing, a coupling impedance matching material, such as silicone, may be placed between the piezoelectric transducer and the surface of tooth to optimize conductance of vibrations to the tooth. In other variations, one or more transducer may be placed along an outer surface of the housing and optionally along one or more teeth.

Aside from transducer and housing assemblies which are positioned along or against one or more teeth, transducer assemblies may be alternatively mounted along a retainer-like structure configured for placement adjacent or along the palate of the user. An arch may extend between coupling portions which are configured to extend from the arch for placement against the lingual surfaces of teeth on opposite sides of the user's dentition. Rather than utilizing transducer assemblies directly upon the teeth, the transducer may be removably or permanently integrated along the arch such that elongational vibration of the transducer conducts the vibrations along the arch for transmission through the coupling portions and into the user's teeth. Alternatively, one of more transducers may be positioned along the arch and actuated to directly conduct vibrations through the user's palatal bone.

BRIEF DESCRIPTION OF THE DRAWINGS

FIG. 7 illustrates another variation of a removable oral appliance supported by an arch and having a microphone unit integrated within the arch.

FIG. 8A illustrates another variation of the removable oral appliance supported by a connecting member which may be positioned along the lingual or buccal surfaces of a patient's row of teeth.

FIGS. 8B to 8E show examples of various cross-sections of the connecting support member of the appliance of FIG. 8A.

FIG. 40A shows a top view of an actuator having a mass attached to an arm which extends from the span of the housing.

FIG. 40B shows a cross-sectional view of the actuator and housing of FIG. 40A.

FIG. 41 shows a top view of an actuator having additional mass elements attached along the housing.

DETAILED DESCRIPTION OF THE INVENTION

An electronic and transducer device may be attached, adhered, or otherwise embedded into or upon a removable oral appliance or other oral device to form an assembly which may conduct audio signals to a user via vibratory conductance through bone for utilization, e.g., as a hearing aid assembly or other audio transmission device. Although described as a hearing aid assembly, the devices and methods herein may be utilized for other auditory treatments or applications and are not limited to use as a hearing aid assembly. Such an oral appliance may be a custom-made device fabricated from a thermal forming process utilizing a replicate model of a dental structure obtained by conventional dental impression methods. The electronic and transducer assembly may receive incoming sounds either directly or through a receiver to process and amplify the signals and transmit the processed sounds via a vibrating transducer element coupled to a tooth or other bone structure, such as the maxillary, mandibular, or palatine bone structure.

Figure 1:
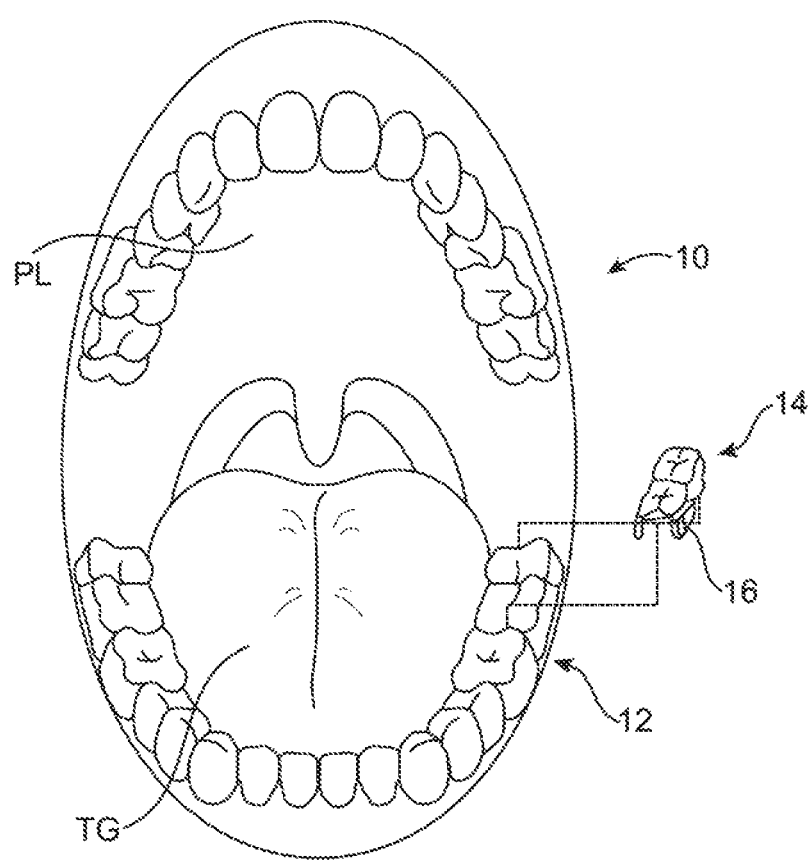
FIG. 1 illustrates the dentition of a patient's teeth and one variation of a hearing aid device which is removably placed upon or against the patient's tooth or teeth as a removable oral appliance.

As shown in FIG. 1, a patient's mouth and dentition 10 is illustrated showing one possible location for removably attaching hearing aid assembly 14 upon or against at least one tooth, such as a molar 12. The patient's tongue TG and palate PL are also illustrated for reference. An electronics and/or transducer assembly 16 may be attached, adhered, or otherwise embedded into or upon the assembly 14, as described below in further detail.

Figure 2A:
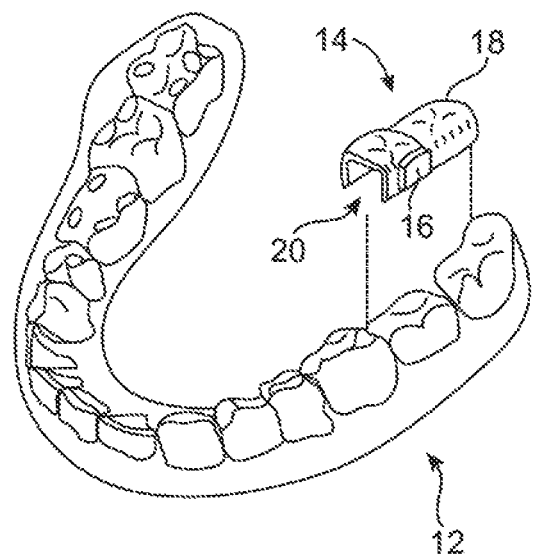
FIG. 2A illustrates a perspective view of the lower teeth showing one exemplary location for placement of the removable oral appliance hearing aid device.

FIG. 2A shows a perspective view of the patient's lower dentition illustrating the hearing aid assembly 14 comprising a removable oral appliance 18 and the electronics and/or transducer assembly 16 positioned along a side surface of the assembly 14. In this variation, oral appliance 18 may be fitted upon two molars 12 within tooth engaging channel 20 defined by oral appliance 18 for stability upon the patient's teeth, although in other variations, a single molar or tooth may be utilized. Alternatively, more than two molars may be utilized for the oral appliance 18 to be attached upon or over. Moreover, electronics and/or transducer assembly 16 is shown positioned upon a side surface of oral appliance 18 such that the assembly 16 is aligned along a buccal surface of the tooth 12; however, other surfaces such as the lingual surface of the tooth 12 and other positions may also be utilized. The figures are illustrative of variations and are not intended to be limiting; accordingly, other configurations and shapes for oral appliance 18 are intended to be included herein.

Figure 2B:
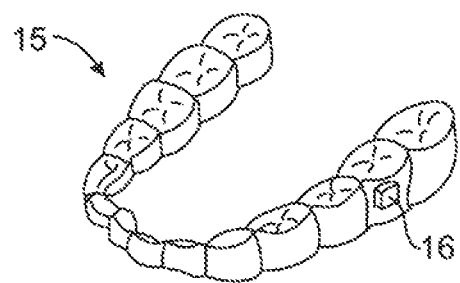
FIG. 2B illustrates another variation of the removable oral appliance in the form of an appliance which is placed over an entire row of teeth in the manner of a mouthguard.

FIG. 2B shows another variation of a removable oral appliance in the form of an appliance 15 which is placed over an entire row of teeth in the manner of a mouthguard. In this variation, appliance 15 may be configured to cover an entire bottom row of teeth or alternatively an entire upper row of teeth. In additional variations, rather than covering the entire rows of teeth, a majority of the row of teeth may be instead be covered by appliance 15. Assembly 16 may be positioned along one or more portions of the oral appliance 15.

Figure 2C:
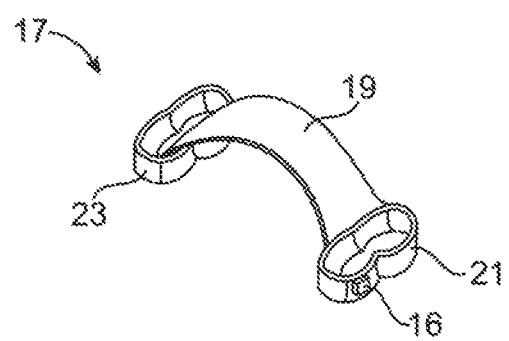
FIG. 2C illustrates another variation of the removable oral appliance which is supported by an arch.

FIG. 2C shows yet another variation of an oral appliance 17 having an arched configuration. In this appliance, one or more tooth retaining portions 21, 23, which in this variation 16 may be placed along the upper row of teeth, may be supported by an arch 19 which may lie adjacent or along the palate of the user. As shown, electronics and/or transducer assembly 16 may be positioned along one or more portions of the tooth retaining portions 21, 23. Moreover, although the variation shown illustrates an arch 19 which may cover only a portion of the palate of the user, other variations may be configured to have an arch which covers the entire palate of the user.

Figure 2D:
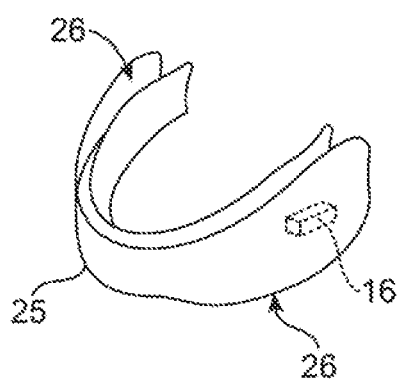
FIG. 2D illustrates another variation of an oral appliance configured as a mouthguard.

FIG. 2D illustrates yet another variation of an oral appliance in the form of a mouthguard or retainer 25 which may be inserted and removed easily from the user's mouth. Such a mouthguard or retainer 25 may be used in sports where conventional mouthguards are worn; however, mouthguard or retainer 25 having assembly 16 integrated therein may be utilized by persons, hearing impaired or otherwise, who may simply hold the mouthguard or retainer 25 via grooves or channels 26 between their teeth for receiving instructions remotely and communicating over a distance.

Generally, the volume of electronics and/or transducer assembly 16 may be minimized so as to be unobtrusive and as comfortable to the user when placed in the mouth. Although the size may be varied, a volume of assembly 16 may be less than 800 cubic millimeters. This volume is, of course, illustrative and not limiting as size and volume of assembly 16 and may be varied accordingly between different users.

Moreover, removable oral appliance 18 may be fabricated from various polymeric or a combination of polymeric and metallic materials using any number of methods, such as computer-aided machining processes using computer numerical control (CNC) systems or three-dimensional printing processes, e.g., stereolithography apparatus (SLA), selective laser sintering (SLS), and/or other similar processes utilizing three-dimensional geometry of the patient's dentition, which may be obtained via any number of techniques. Such techniques may include use of scanned dentition using intra-oral scanners such as laser, white light, ultrasound, mechanical three-dimensional touch scanners, magnetic resonance imaging (MRI), computed tomography (CT), other optical methods, etc.

In forming the removable oral appliance 18, the appliance 18 may be optionally formed such that it is molded to fit over the dentition and at least a portion of the adjacent gingival tissue to inhibit the entry of food, fluids, and other debris into the oral appliance 18 and between the transducer assembly and tooth surface. Moreover, the greater surface area of the oral appliance 18 may facilitate the placement and configuration of the assembly 16 onto the appliance 18.

Additionally, the removable oral appliance 18 may be optionally fabricated to have a shrinkage factor such that when placed onto the dentition, oral appliance 18 may be configured to securely grab onto the tooth or teeth as the appliance 18 may have a resulting size slightly smaller than the scanned tooth or teeth upon which the appliance 18 was formed. The fitting may result in a secure interference fit between the appliance 18 and underlying dentition.

Figure 3:
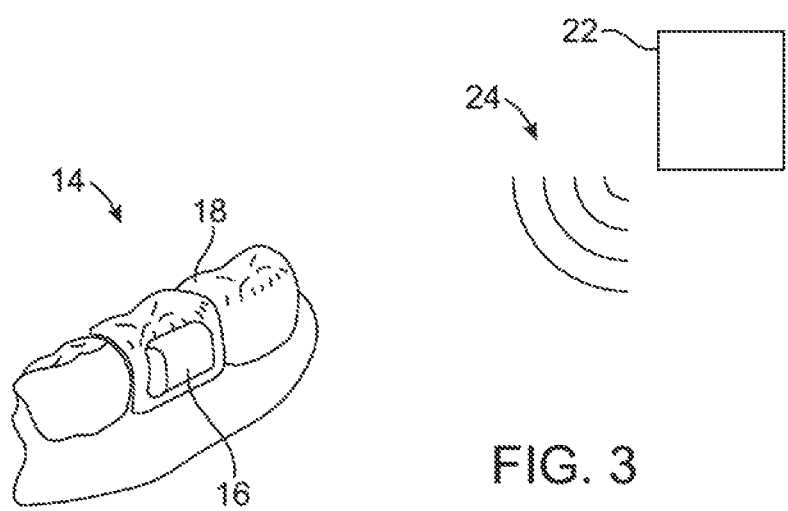
FIG. 3 illustrates a detail perspective view of the oral appliance positioned upon the patient's teeth utilizable in combination with a transmitting assembly external to the mouth and wearable by the patient in another variation of the device.

In one variation, with assembly 14 positioned upon the teeth, as shown in FIG. 3, an extra-buccal transmitter assembly 22 located outside the patient's mouth may be utilized to receive auditory signals for processing and transmission via a wireless signal 24 to the electronics and/or transducer assembly 16 positioned within the patient's mouth, which may then process and transmit the processed auditory signals via vibratory conductance to the underlying tooth and consequently to the patient's inner ear.

The transmitter assembly 22, as described in further detail below, may contain a microphone assembly as well as a transmitter assembly and may be configured in any number of shapes and forms worn by the user, such as a watch, necklace, lapel, phone, belt-mounted device, etc.

Figure 4:
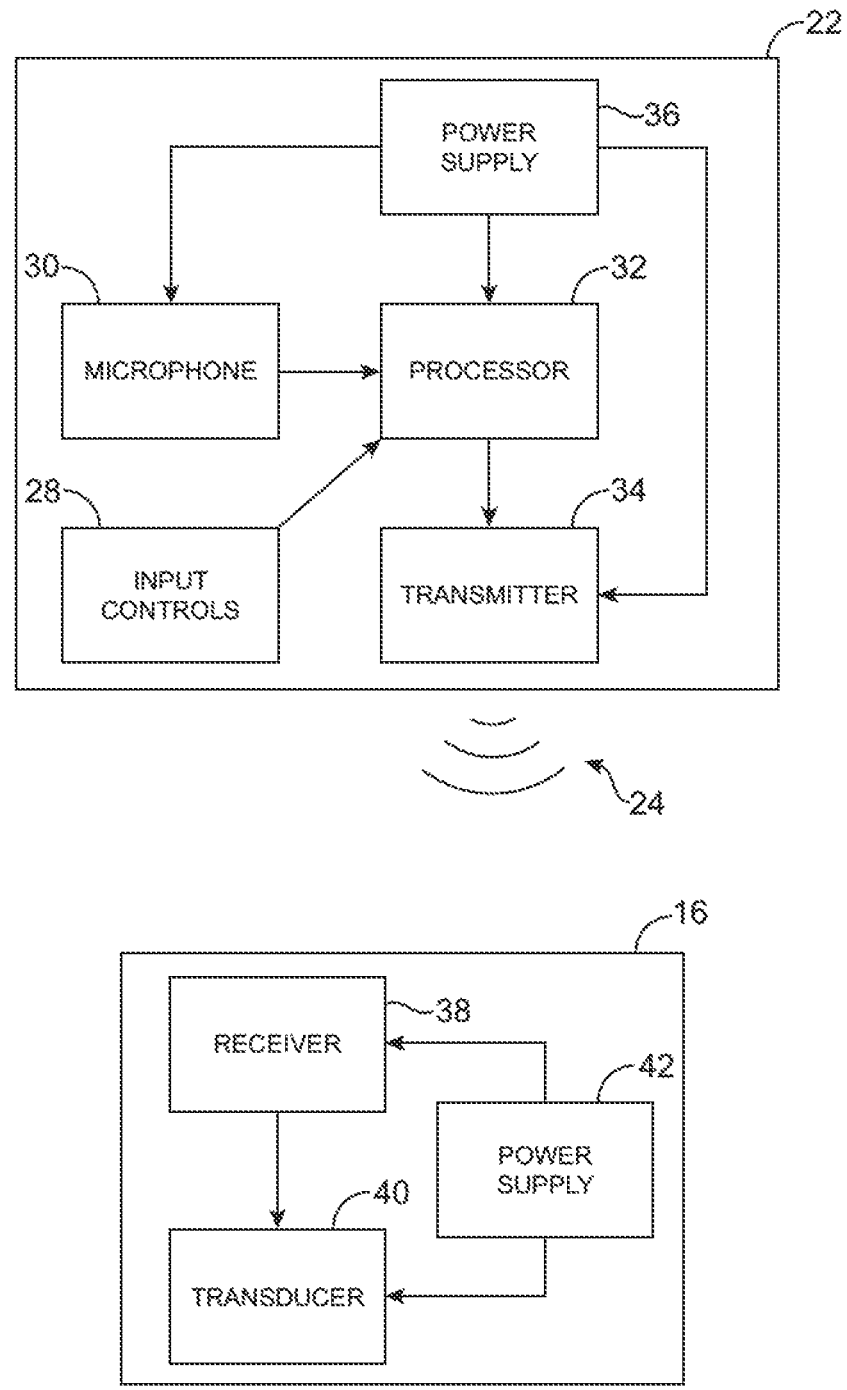
FIG. 4 shows an illustrative configuration of one variation of the individual components of the oral appliance device having an external transmitting assembly with a receiving and transducer assembly within the mouth.

FIG. 4 illustrates a schematic representation of one variation of hearing aid assembly 14 utilizing an extra-buccal transmitter assembly 22, which may generally comprise microphone or microphone array 30 (referred to "microphone 30" for simplicity) for receiving sounds and which is electrically connected to processor 32 for processing the auditory signals. Processor 32 may be connected electrically to transmitter 34 for transmitting the processed signals to the electronics and/or transducer assembly 16 disposed upon or adjacent to the user's teeth. The microphone 30 and processor 32 may be configured to detect and process auditory signals in any practicable range, but may be configured in one variation to detect auditory signals ranging from, e.g., 50 Hertz to 20,000 Hertz.

With respect to microphone 30, a variety of various microphone systems may be utilized. For instance, microphone 30 may be a digital, analog, and/or directional type microphone. Such various types of microphones may be interchangeably configured to be utilized with the assembly, if so desired. Moreover, various configurations and methods for utilizing multiple microphones within the user's mouth may also be utilized, as further described below.

Power supply 36 may be connected to each of the components in transmitter assembly 22 to provide power thereto. The transmitter signals 24 may be in any wireless form utilizing, e.g., radio frequency, ultrasound, microwave, Blue Tooth® (BLUETOOTH SIG, INC., Bellevue, Wash.), etc. for transmission to assembly 16. Assembly 22 may also optionally include one or more input controls 28 that a user may manipulate to adjust various acoustic parameters of the electronics and/or transducer assembly 16, such as acoustic focusing, volume control, filtration, muting, frequency optimization, sound adjustments, and tone adjustments, etc.

The signals transmitted 24 by transmitter 34 may be received by electronics and/or transducer assembly 16 via receiver 38, which may be connected to an internal processor for additional processing of the received signals. The received signals may be communicated to transducer 40, which may vibrate correspondingly against a surface of the tooth to conduct the vibratory signals through the tooth and bone and subsequently to the middle ear to facilitate hearing of the user. Transducer 40 may be configured as any number of different vibratory mechanisms. For instance, in one variation, transducer 40 may be an electromagnetically actuated transducer. In other variations, transducer 40 may be in the form of a piezoelectric crystal having a range of vibratory frequencies, e.g., between 250 to 15,000 Hz.

Power supply 42 may also be included with assembly 16 to provide power to the receiver, transducer, and/or processor, if also included. Although power supply 42 may be a simple battery, replaceable or permanent, other variations may include a power supply 42 which is charged by inductance via an external charger. Additionally, power supply 42 may alternatively be charged via direct coupling to an alternating current (AC) or direct current (DC) source. Other variations may include a power supply 42 which is charged via a mechanical mechanism, such as an internal pendulum or slidable electrical inductance charger as known in the art which is actuated via, motions of the jaw and/or movement for translating the Mechanical motion into stored electrical energy for charging power supply 42.

Figure 5:
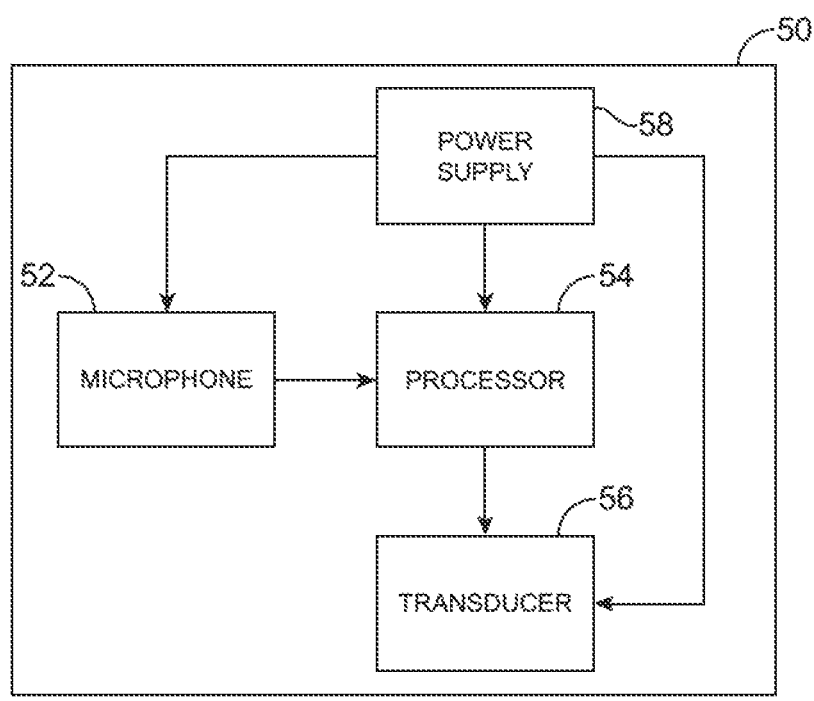
FIG. 5 shows an illustrative configuration of another variation of the device in which the entire assembly is contained by the oral appliance within the user's mouth.

In another variation of assembly 16, rather than utilizing an extra-buccal transmitter, hearing aid assembly 50 may be configured as an independent assembly contained entirely within the user's mouth, as shown in FIG. 5. Accordingly, assembly 50 may include at least one internal microphone 52 in communication with an on-board processor 54. Internal microphone 52 may comprise any number of different types of microphones, as described below in further detail. At least one processor 54 may be used to process any received auditory signals for filtering and/or amplifying the signals and transmitting them to transducer 56, which is in vibratory contact against the tooth surface. Power supply 58, as described above, may also be included within assembly 50 for providing power to each of the components of assembly 50 as necessary.

In order to transmit the vibrations corresponding to the received auditory signals efficiently and with minimal loss to the tooth or teeth, secure mechanical contact between the transducer and the tooth is ideally maintained to ensure efficient vibratory communication. Accordingly, any number of mechanisms may be utilized to maintain this vibratory communication.

Figure 6:
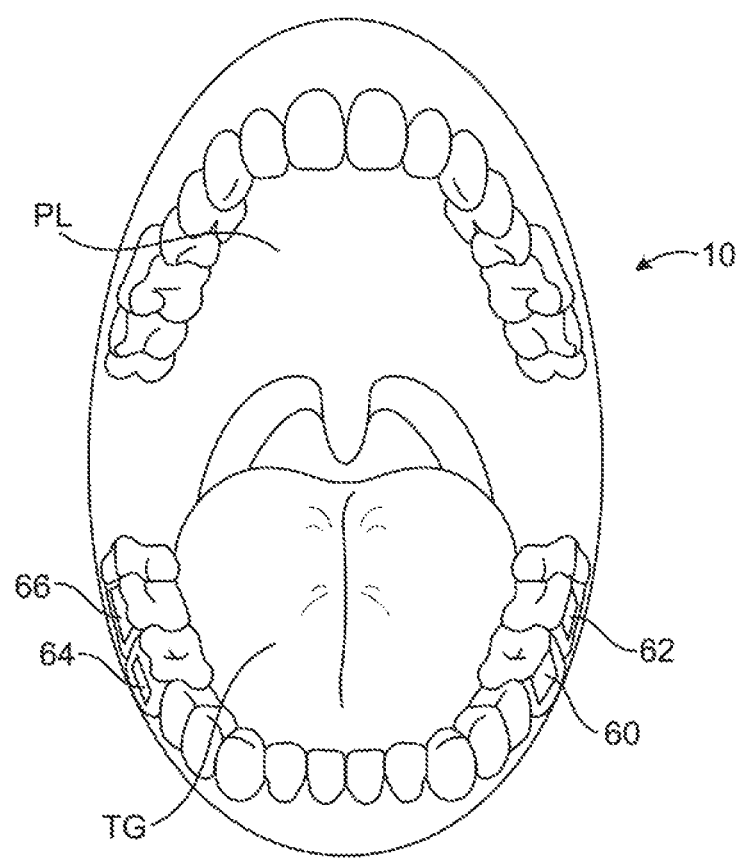
FIG. 6 illustrates an example of how multiple oral appliance hearing aid assemblies or transducers may be placed on multiple teeth throughout the patient's mouth.

For any of the variations described above, they may be utilized as a single device or in combination with any other variation herein, as practicable, to achieve the desired hearing level in the user. Moreover, more than one oral appliance device and electronics and/or transducer assemblies may be utilized at any one time. For example, FIG. 6 illustrates one example where multiple transducer assemblies 60, 62, 64, 66 may be placed on multiple teeth. Although shown on the lower row of teeth, multiple assemblies may alternatively be positioned and located along the upper row of teeth or both rows as well. Moreover, each of the assemblies may be configured to transmit vibrations within a uniform frequency range. Alternatively in other variations, different assemblies may be configured to vibrate within overlapping or non-overlapping frequency ranges between each assembly. As mentioned above, each transducer 60, 62, 64, 66 can be programmed or preset for a different frequency response such that each transducer may be optimized for a different frequency response and/or transmission to deliver a relatively high-fidelity sound to the user.

Moreover, each of the different transducers 60, 62, 64, 66 can also be programmed to vibrate in a manner which indicates the directionality of sound received by the microphone worn by the user. For example, different transducers positioned at different locations within the user's mouth can vibrate in a specified manner by providing sound or vibrational queues to inform the user which direction a sound was detected relative to an orientation of the user, as described in further detail below. For instance, a first transducer located, e.g. on a user's left tooth, can be programmed to vibrate for sound detected originating from the user's left side. Similarly, a second transducer located, e.g., on a user's right tooth, can be programmed to vibrate for sound detected originating from the user's right side. Other variations and queues may be utilized as these examples are intended to be illustrative of potential variations.

FIG. 7 illustrates another variation 70 which utilizes an arch 19 connecting one or more tooth retaining portions 21, 23, as described above. However, in this variation, the microphone unit 74 may be integrated within or upon the arch 19 separated from the transducer assembly 72. One or more wires 76 routed through arch 19 may electrically connect the microphone unit 74 to the assembly 72. Alternatively, rather than utilizing a wire 76, microphone unit 74 and assembly 72 may be wirelessly coupled to one another, as described above.

FIG. 8A shows another variation 80 which utilizes a connecting member 82 which may be positioned along the lingual or buccal surfaces of a patient's row of teeth to connect one or more tooth retaining portions 21, 23. Connecting member 82 may be fabricated from any number of non-toxic materials, such stainless steel, Nickel, Platinum, etc. and affixed or secured 84, 86 to each respective retaining portions 21, 23. Moreover, connecting member 82 may be shaped to be as non-obtrusive to the user as possible. Accordingly, connecting member 82 may be configured to have a relatively low-profile for placement directly against the lingual or buccal teeth surfaces. The cross-sectional area of connecting member 82 may be configured in any number of shapes so long as the resulting geometry is non-obtrusive to the user. FIG. 8B illustrates one variation of the cross-sectional area which may be configured as a square or rectangle 90. FIG. 8C illustrates another connecting member geometry configured as a semi-circle 92 where the flat portion may be placed against the teeth surfaces. FIGS. 8D and 8E illustrate other alternative shapes such as an elliptical shape 94 and circular shape 96. These variations are intended to be illustrative and not limiting as other shapes and geometries, as practicable, are intended to be included within this disclosure.

Figure 9:
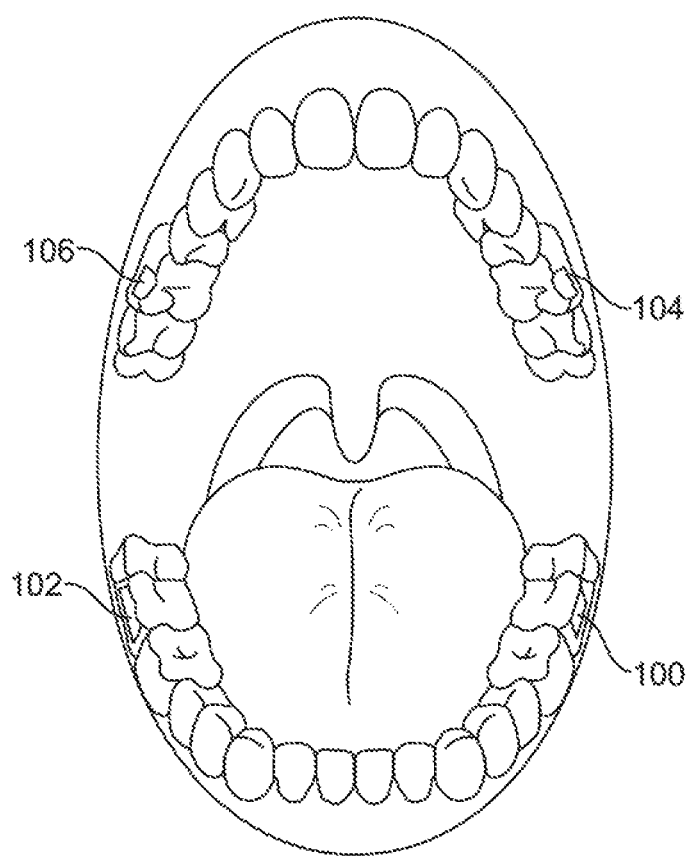
FIG. 9 shows yet another variation illustrating at least one microphone and optionally additional microphone units positioned around the user's mouth and in wireless communication with the electronics and/or transducer assembly.

In yet another variation for separating the microphone from the transducer assembly, FIG. 9 illustrates another variation where at least one microphone 102 (or optionally any number of additional microphones 104, 106) may be positioned within the mouth of the user while physically separated from the electronics and/or transducer assembly 100. In this manner, the one or optionally more microphones 102, 104, 106 may be wirelessly or by wire coupled to the electronics and/or transducer assembly 100 in a manner which attenuates or eliminates feedback from the transducer, also described in further detail below.

In utilizing multiple transducers and/or processing units, several features may be incorporated with the oral appliance (s) to effect any number of enhancements to the quality of the conducted vibratory signals and/or to emulate various perceptual features to the user to correlate auditory signals received by a user for transmitting these signals via sound conduction through teeth or bone structures in and/or around the mouth. Examples of various processing methods and systems for simulating directionality as well as for processing algorithms for filtering out undesirable signals, among other features, are shown and described in further detail in U.S. patent application Ser. No. 11/672,239 filed Feb. 7, 2007, which is incorporated herein by reference in its entirety. The features shown and described may be utilized with any of the variations described herein and in any number of combinations as practicable.

Figure 10A:
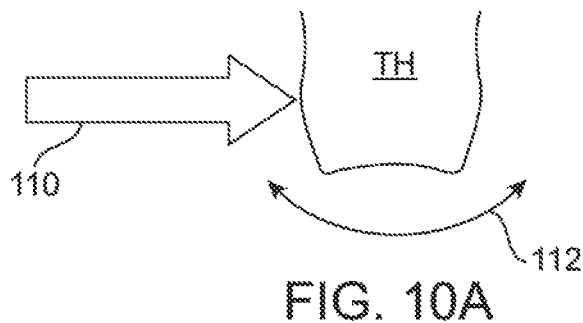
FIGS. 10A to 10C illustrate some of the various approaches for oscillating a patient's tooth or teeth (from a single surface, both surfaces, or against the occlusal surface, respectively) when conducting audio signals to the user.
Figure 10B:
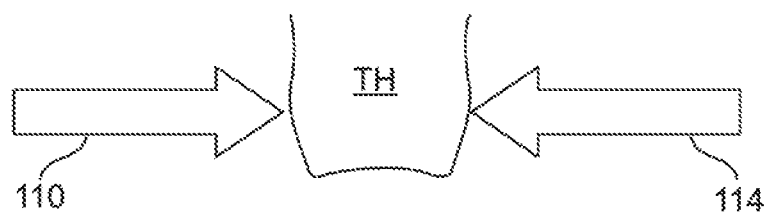
Figure 10C:
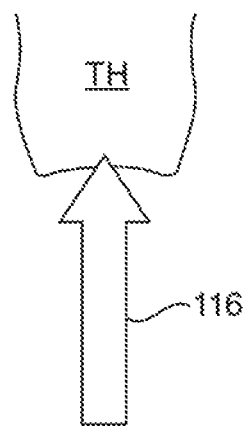

In transmitting the vibrations generated from auditory signals received by the user, the one or more transducers may be positioned relative to the tooth or teeth as well as relative to the housing itself retaining the one or more transducers. Generally, an oscillating force 110 may be presented along a single surface of a user's tooth or teeth TH such that the tooth vibrates 112, as shown illustratively in FIG. 10A, and conducts the vibrations through the skull. In another variation, FIG. 10B shows how an additional oscillating force 114 may be imparted against the tooth TH on an opposite surface from where force 110 is imparted. In this mode, the impedance presented to the actuator is relatively larger than the impedance presented in FIG. 10A thereby potentially requiring less displacement by the actuator, e.g., about 40 dB less relatively. In yet another variation, FIG. 10C shows how an oscillating force 116 may be presented against an occlusal surface of the tooth TH. In this variation, the vibrational transmission path is relatively clear and direct through the tooth TH and to the skull of the user.

As mentioned above, the transducer utilized in the actuator assembly may be an electromagnetic transducer or a piezoelectric transducer. Piezoelectric transducers in particular may be used in various configurations due in part to the various vibrational modes which may be utilized to transmit the acoustic signals as vibrations through a tooth or teeth. Some of the native vibrational modes of a piezoelectric transducer which may be utilized in an actuator assembly described herein are illustrated in FIGS. 11A to 11C.

Figure 11A:
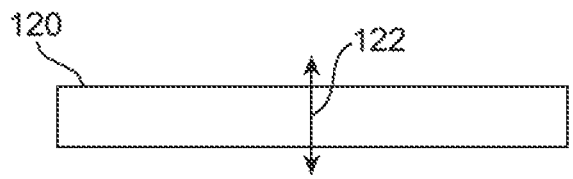
FIGS. 11A to 11C show examples of piezoelectric structures and their various modes of vibration by which they can be utilized, for example, thickness mode, elongational mode, and shear mode, respectively.
Figure 11B:
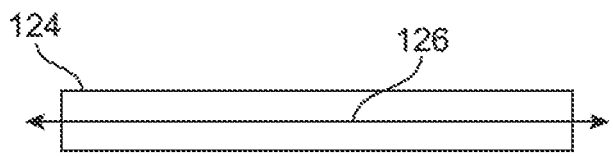
Figure 11C:
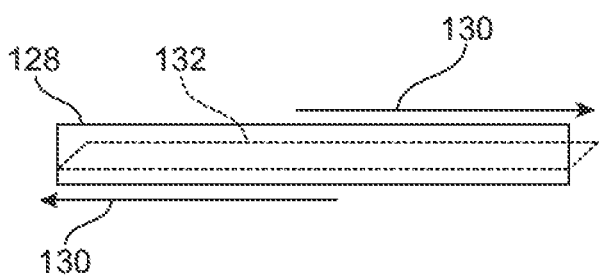

FIG. 11A shows a representative piezoelectric transducer having dipoles induced within the molecular or crystal structure of the material which align with an electric field applied across the transducer 120. This alignment of molecules causes the transducer 120 to change dimensions and vibrate accordingly in the direction 122. Alternatively, transducer 124 may be configured to utilize the dimensional changes in the elongational direction 126 along a length of transducer 124, as indicated in FIG. 11B. In yet another alternative, transducer 128 may have an electric field and dipole orientation which results in the transducer 128 exhibiting shear mode where opposing surfaces of transducer 128 may vibrate in opposing directions 130. The transducer 128 may thus oscillate between its non-deformed configuration and a sheared configuration 132, as indicated in FIG. 11C.

Figure 12A:
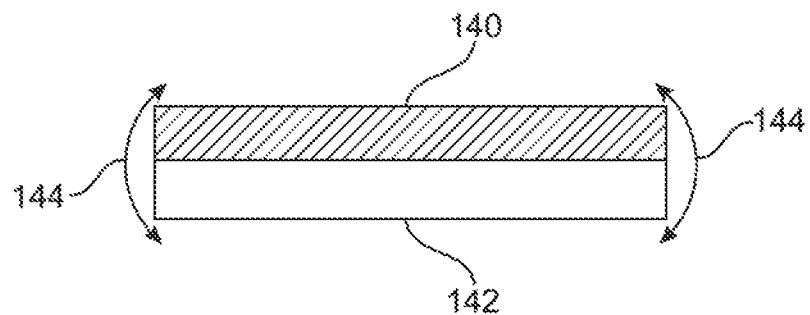
FIGS. 12A and 12B show additional examples of composite piezoelectric structures utilizing unimorph and/or bimorph structures and symmetric composite structures, respectively.
Figure 12B:
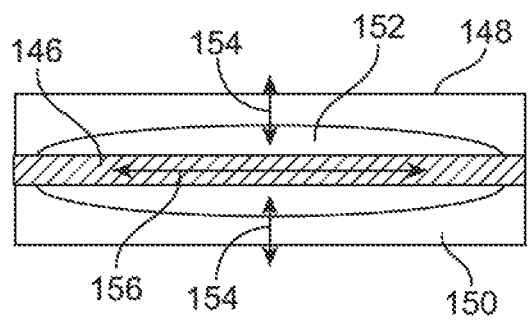

In other configurations, the piezoelectric transducer may be utilized within actuator assemblies. These assemblies change the impedance of the actuator and typically generate larger displacements but have relatively lower stiffness and resonance values. For instance, FIG. 12A illustrates an example of a piezoelectric transducer 140 which may be coupled to either a second transducer or an elastic material 142 to form a bender configuration, e.g., unimorph or bimorph configuration. Upon application of an electric field, the composite transducer may oscillate in a bending or flexing mode 144. In yet another composite mode configuration, FIG. 12B illustrates an example of a moonie or cymbal type transducer which are typically symmetric in shape and which may be utilized in an actuator assembly described herein. Generally, such composite transducers utilize a single layer or multilayer form piezoelectric transducer 146 which is sandwiched between opposing endcaps 148, 150. Each endcap 148, 150 may form a cavity, such as a crescent-shaped cavity 152, along an inner surface and serves as a mechanical transformer for converting and amplifying lateral displacements 156 of the transducer 146 into an axial motion 154 of the endcaps 148, 150.

Any number of transducers may be utilized for such particular applications. For instance, low voltage multi-layer piezoelectric transducers manufactured by Morgan Electro Ceramics Ltd. (Wrexham, England) may be utilized for the applications described herein.

Figure 13:
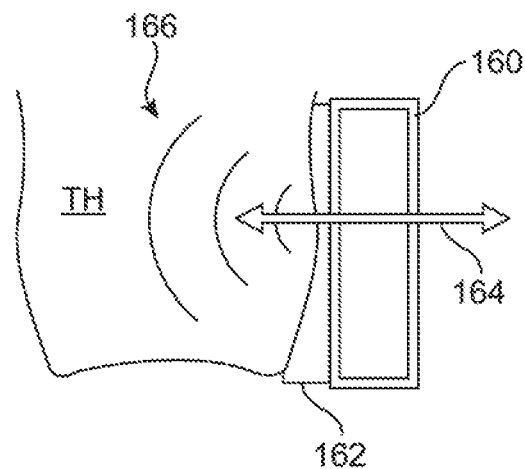
FIG. 13 illustrates one example of how an actuator may be positioned to oscillate to deliver acoustic energy through a user's tooth or teeth.

In transmitting the vibrational energy from the transducer to the user, the actuator assembly 160 may be positioned against the tooth or teeth TH with an impedance matching layer 162 placed therebetween, as shown in FIG. 13. The impedance matching layer 162 may be utilized to improve coupling and optimize the transmission of vibrational energy 166 from the actuator 160 into the tooth TH and to optimize the transmission into the tooth TH of any reflected vibrations. In addition, the coupling layer will aid in fit and ease of insertion.

Figure 14A:
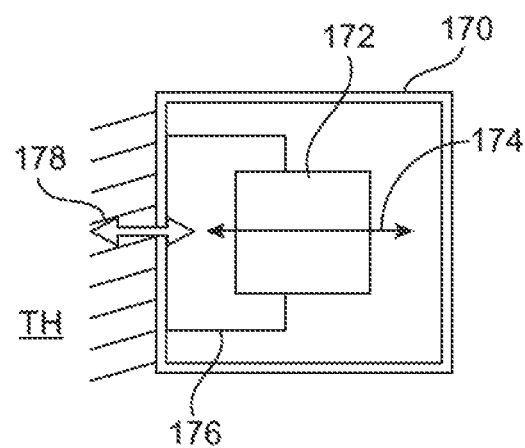
FIG. 14A schematically illustrates an example of an actuator utilizing a mass to generate a sufficient actuation force.

One variation of an actuator assembly which may be utilized in the housing is shown illustratively in FIG. 14, which shows an actuator assembly 170 enclosing a representative actuator 176 having a mass 172 coupled thereto. Actuator 176 may be either an electromagnetic or piezoelectric transducer depending upon the desired results. Mass 176 may be of a size and weight sufficient to generate forces such that an oscillatory motion 174 of mass 172 imparted by actuator 176 leads to a reaction force 178 imparted to the tooth TH. Use of a separate mass 172 may also be useful in generating a sufficient reaction force 178 even if a resonance of the assembly itself is in a frequency range of interest. The mass may be comprised of a component fabricated to be the mass element or the mass may be comprised of other components of the system such as, e.g., the associated electronics, battery, charging system, etc.

Figure 14B:
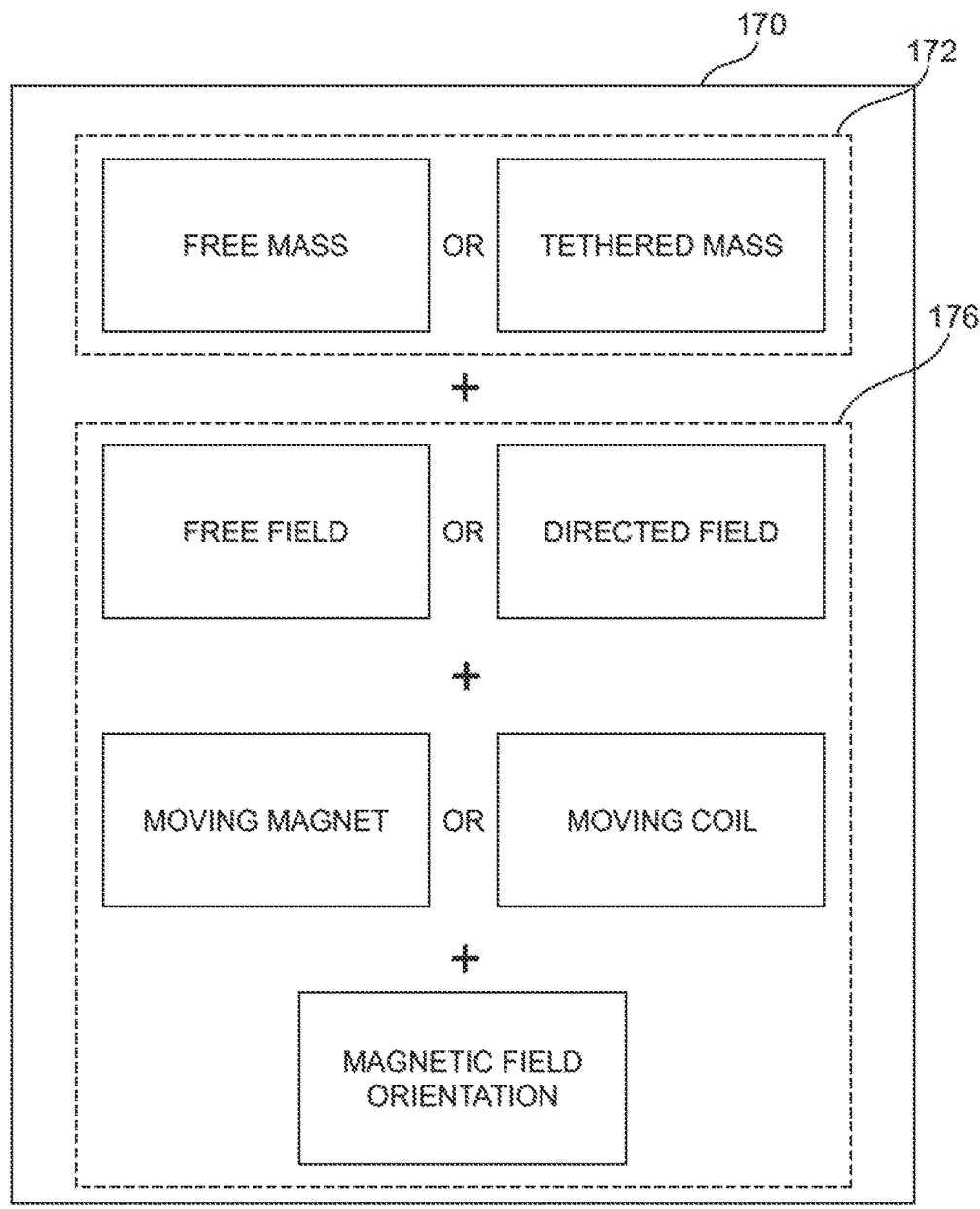
FIG. 14B shows some of the various combinations for an electromagnetic transducer assembly utilized with the housing for placement along or against a user's dentition.

In configurations utilizing an electromagnetic actuator assembly, there are a number of various architectures which may be utilized. For instance, FIG. 14B shows some of the various combinations for an electromagnetic transducer assembly utilized with the housing for placement along or against a user's dentition. The mass 172 utilized may be either a free mass which may be a separable component aligned within the assembly or a tethered mass which is coupled to the housing via a mechanical member or mechanism. Aside from the mass, the magnetic field may be configured as either a natural field which follows a natural path or a directed field which is guided through, e.g., a magnetic circuit. Additionally, the moving mass element may be configured as either a permanent moving magnet or as a current carrying moving coil. Finally, the magnetic field orientation may be varied depending upon the configuration of the magnet and mass. Any combination of these elements may be utilized for configuring an electromagnetic transducer to achieve a desired result, e.g., the combination of a free mass element 172 configured as a moving magnet and contained within a directed field may be utilized.

Figure 15:
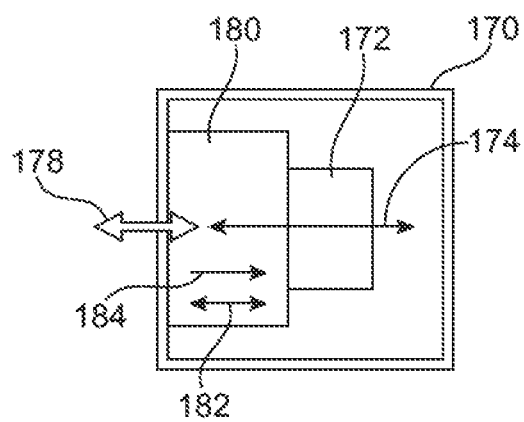
FIG. 15 schematically illustrates a variation of an actuator utilizing a piezoelectric transducer having a mass coupled thereto.
Figure 16:
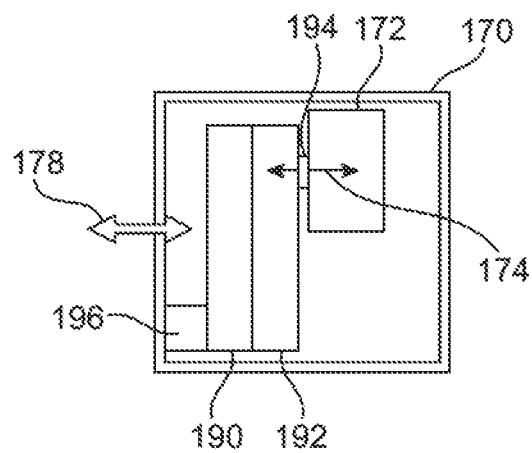
FIG. 16 schematically illustrates another variation of an actuator having a piezoelectric unimorph or bimorph transducer configured into a beam anchored to the housing.

FIG. 15 illustrates a variation of the actuator assembly which utilizes a mass 172 coupled to a piezoelectric transducer 180. Upon application of an electric field 182, the induced dipole 184 in the piezoelectric material may align to impart an oscillatory motion 174 upon mass 172. FIG. 16 shows yet another variation where actuator assembly 170 may enclose a composite transducer, such as a bending unimorph or bimorph type transducer having one or more transducer elements 190, 192 coupled together. The actuator assembly may be coupled to the assembly enclosure 170 via a single anchoring point 196 near or at a first end of the transducer beam assembly. Alternatively, the actuator assembly may omit anchor 196 entirely and one edge or end of transducer elements 190, 192 may be anchored directly to the housing itself. Mass 172 may be attached to the composite transducer at a second end of the transducer beam assembly also via a single anchoring point 194 such that when the one or more transducers 190, 192 are activated to oscillate, a vibrational motion 174 may be imparted to mass 172 via anchor 194 such that the resulting reaction force 178 is sufficiently transmitted to the underlying tooth or teeth. The mass 172 secured at anchor 194 may extend away from or towards anchor 196. It may be advantageous to have the mass 172 above or below the beam (e.g., transducers 190, 192) as the resulting moment applied to the beam by the mass 172 during actuation may develop advantageous moments for various applications. The anchor point 194 may also be on the end of the beam (a point down the length of the beam from 190).

Figure 17:
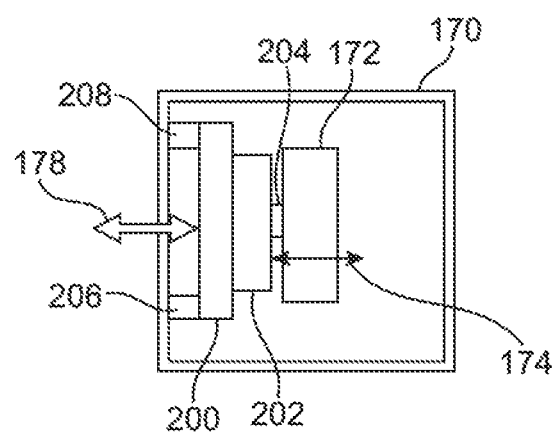
FIG. 17 schematically illustrates yet another variation utilizing an actuator having a symmetric (e.g., circularly, cylindrically, bilaterally) piezoelectric bender configuration.

In yet another variation, FIG. 17 shows an actuator assembly 170 utilizing a symmetric (e.g., circularly or bilaterally symmetric) bender transducer assembly having one or more transducers 200, 202 attached to one another. The one or more transducers 200, 202 may be the same diameter or a second transducer 202 may have a diameter which is less than a diameter of the first transducer 200. Mass 172 may be coupled to second transducer 202 via anchoring point 204 along its central axis, in which case first transducer 200 may be coupled to assembly enclosure 170 via multiple anchors 206, 208 or via it circular anchoring element around a circumference of transducer 200.

Figure 18:
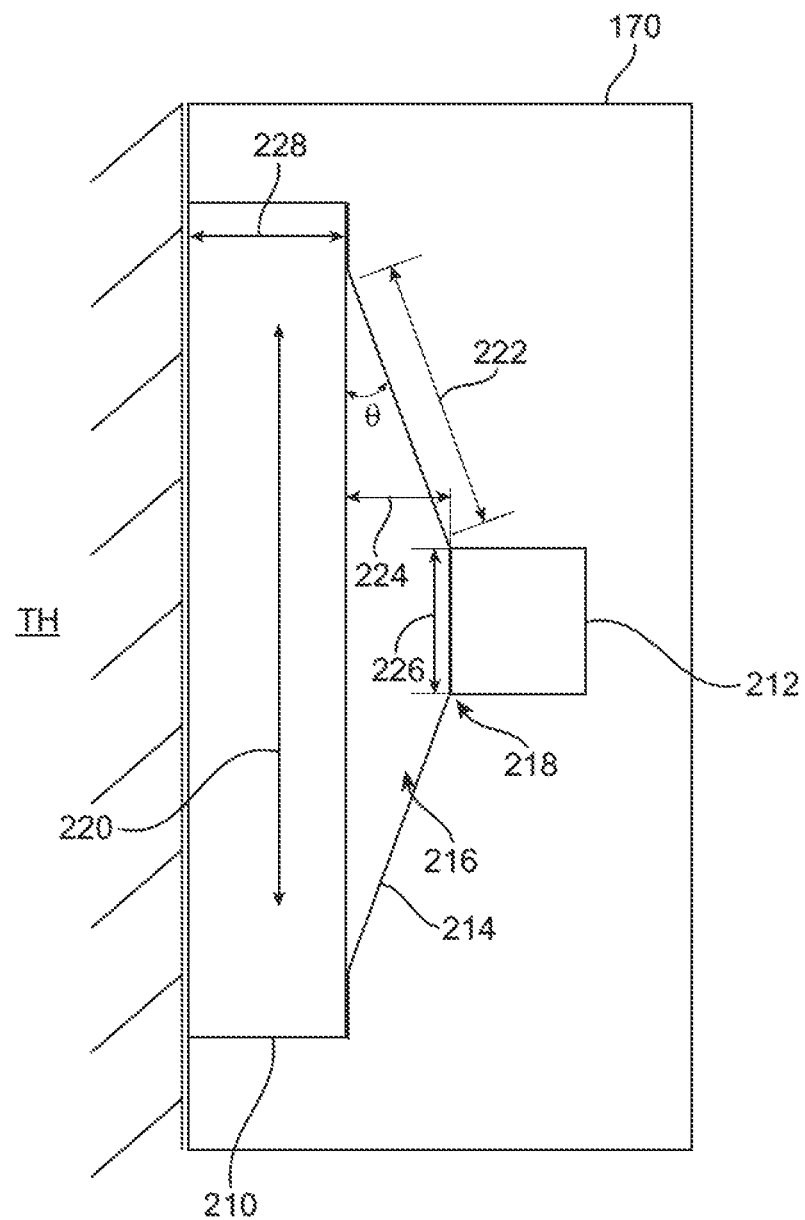
FIG. 18 schematically illustrates another variation of an actuator utilizing a cap-based configuration.

Another variation is illustrated in the actuator assembly of FIG. 18, which shows a piezoelectric cap-based design. Such a variation may utilize a piezoelectric transducer 210 having a thickness 228 and which is configured to oscillate in an elongational mode 220. Mass 212 having a thickness and a width 226 may be positioned at a distance 224 away from the transducer surface via a cap member 214 or support members having a length 222 and forming an angle, θ, relative to the transducer 210. Cap 214 may be fabricated from a metal to be symmetric, e.g., circularly or bilaterally symmetric, and may define a cavity 216 between transducer 210 and cap 214. As piezoelectric transducer 210 is actuated to oscillate in its elongational direction 220, cap 214 may be forced to flex while vibrating mass 212 in a direction transverse to the elongational direction 220, thereby creating the reaction force for transmission into the user's tooth or teeth. Because of the flexing of mass 212 relative to transducer 210 and cap 214, the attachment 218 between mass 212 and cap 214 may be configured into a joint to allow for the relative movement. Any number of pivoting or bending mechanisms may be utilized, e.g., living hinges, silicone glue joints, etc. Alternatively, the device may be configured such that the mass 212 is connected to the piezoelectric transducer 210 and the reaction force is transmitted to the load through the cap 214 itself. Additionally, the device may have a top and a bottom cap which are placed on opposite sides of the transducer 210. In this variation, the mass 212 may be attached to either top or bottom cap while the force is transmitted to the load through the remaining cap.

Figure 19:
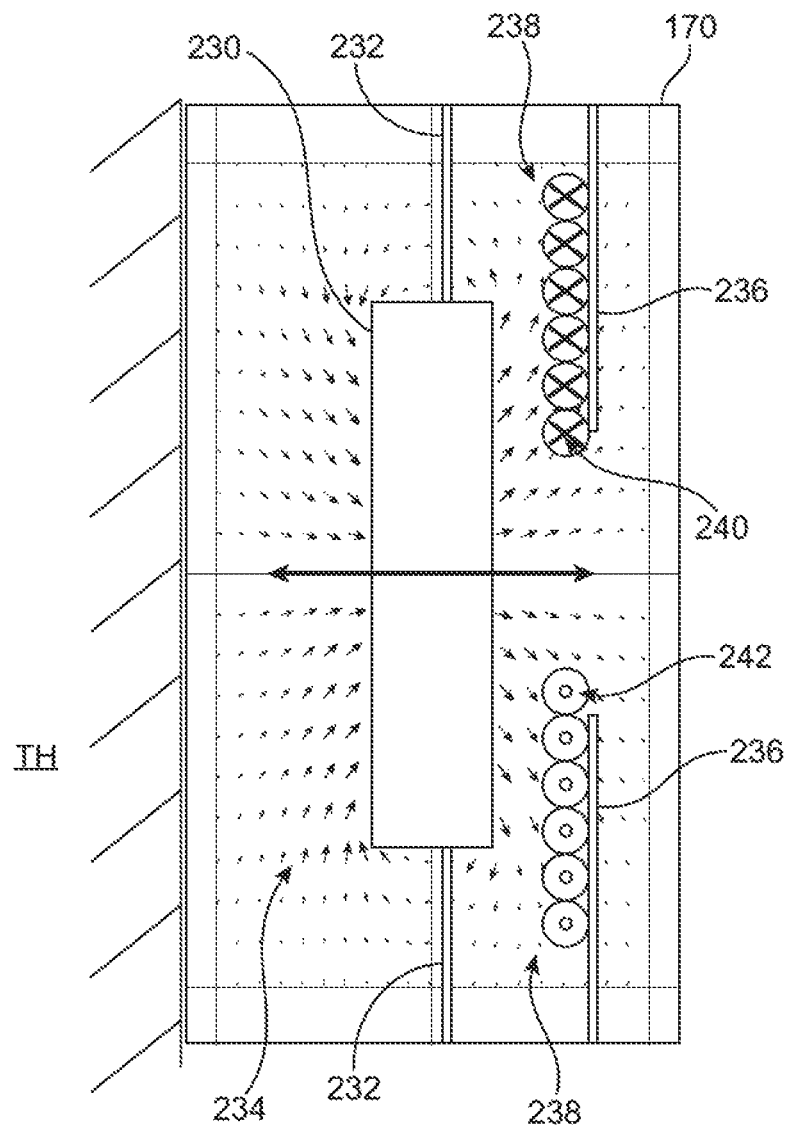
FIG. 19 schematically illustrates another variation of an actuator utilizing an electromagnetic vibration mechanism.

FIG. 19 shows another variation of an actuator assembly utilizing the force between a magnet contained within the assembly housing 170 and an applied current to control the movement of a mass. Magnet 230 may be a permanent magnet suspended via one or more flexible support members 232 held in proximity to one or more coils 238. Separate coils may be positioned on either side of magnet 230 such that the device is symmetric with respect to the magnet 230. Such extra coils may improve the force output linearity of the device. Moreover, magnet 230 may additionally function as the mass or a separate mass element may be attached to magnet 230. Coils 238 may be held adjacent to magnet 230 via one or more relatively rigid support members 236 and they may carry a current 240, 242 which is correlated to the received and processed auditory signals. When a current is passed through the coils 238 in the presence of a magnetic field 234 generated by magnet 230, magnet 230 may vibrate accordingly while suspended by support members 232 to impart the vibrational reaction force to the tooth TH.

Regardless of the specific transducer design, the resulting functional transmitted output level is desirably constant over a specified frequency range which is below uncomfortable loudness and vibration levels over the entire frequency range.

Figure 20:
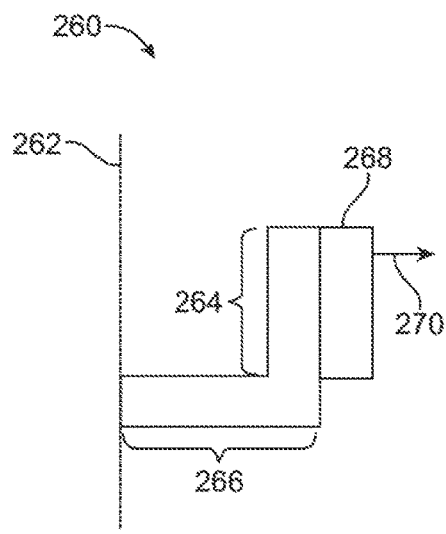
FIG. 20 illustrates a model of an actuator mounted on an housing.

In determining the parameters for the desired amount of deflection generated by the transducer assembly as well as for design parameters for the housing assembly, the entire system 260 may be modeled as spring members coupled in series. As illustrated in FIG. 20, half of the system 260 divided along the symmetrical line 262 may be modeled as an arm member 264 and bottom or span member 266. Transducer assembly 268 and its generated vibrational force 270 may be coupled along arm member 264, in this particular example. Although each member 264, 266 may have its own compliance value, the entire system compliance may be determined by a sum of the individual compliance values.

Figure 21:
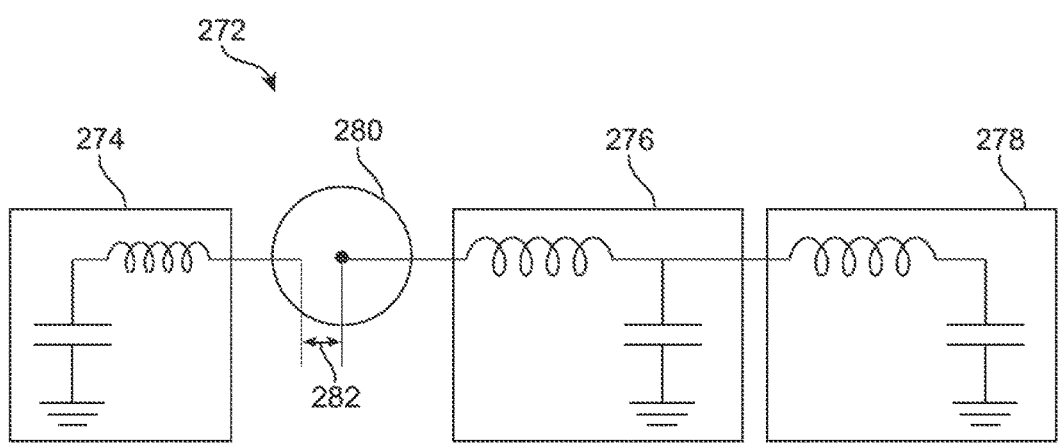
FIG. 21 illustrates an idealized model of the actuator of FIG. 20.

FIG. 21 illustrates a schematic representation 272 of a transducer and housing assembly where the inductor-capacitor circuit 274 represents the equivalent value from the tooth TH, circuit 276 represents the equivalent value from arm member 264, circuit 278 represents the equivalent value from span member 266, and schematic 280 represents the coupled area between the arm member 264 and tooth TH and the amount of transducer deflection or throw 282. The total throw 282 of the transducer 268 may be divided between the tooth TH and the housing where the softer of the two deflects the most. The amount of force 270 transmitted by the transducer 268 may be determined by the stiffness of the tooth and the amount of displacement at the tooth TH. Thus, the softer the housing material relative to the tooth TH, the less displacement may be transmitted thereby such that the amount of throw 282 that should be increased.

The span member 266 of the housing assembly is desirably stiff to function as a platform which allows the transducer assembly 268 to generate a sufficient amount of force for transmission into the tooth or teeth TH. Moreover, although any number of transducer designs may be utilized, as shown herein, multilayer piezoelectric transducers may be particularly effective in multiplying the voltage output. Moreover, to maintain a constant level of output force generated by the transducer assembly, resonance values of the housing and transducer assemblies may be designed such that they occur outside a desirable frequency range of interest, e.g., 250 Hz to 10,000 Hz, by optimizing parameters of the housing, such as a thickness of the span member 266, to alter a resonant frequency of the system.

Figure 22:
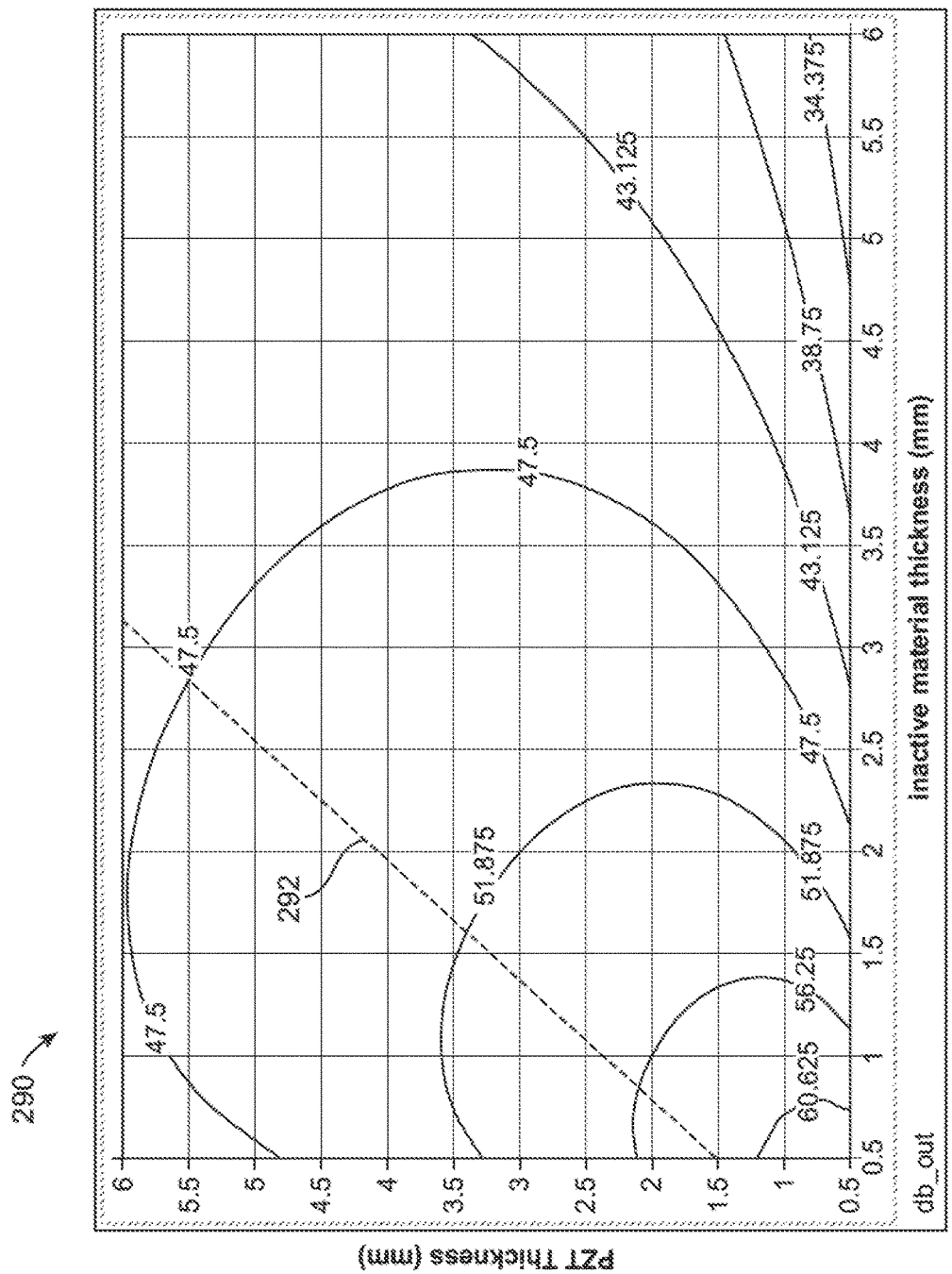
FIG. 22 shows an example of a plot which may be utilized for determining an actuator output as a function of a wall thickness of the housing and a thickness of a piezoelectric transducer.

Plot 290 of FIG. 22 illustrates in one example the relationship of the dB output as a function of the thickness of the housing and a thickness of the piezoelectric transducer material. The contour lines indicate equal dB output values where line 292 represents optimal output values for a given device size. Accordingly, for a given thickness of a piezoelectric transducer material, e.g., 2 mm thick, increases in the thickness of the housing material leads to nominal increases in output levels whereas increases in the stiffness of the span member may lead to relatively greater output values.

Figure 23A:
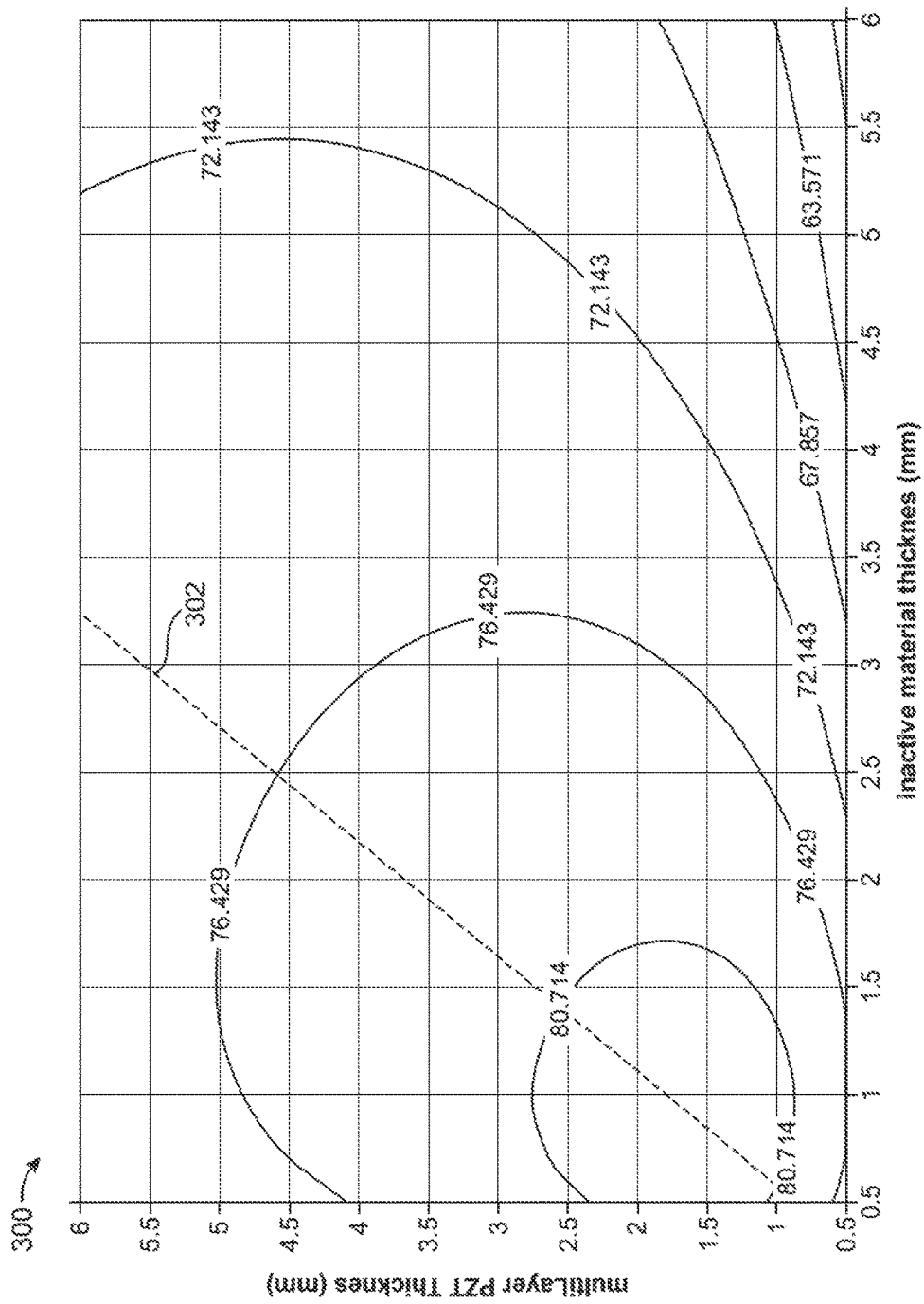
FIGS. 23A and 23B show additional examples of plots which may be utilized for determining actuator output as a function of wall thickness of the housing and piezoelectric transducer thickness for a housing which may be positioned along a proximal surface of a user's tooth.
Figure 23B:
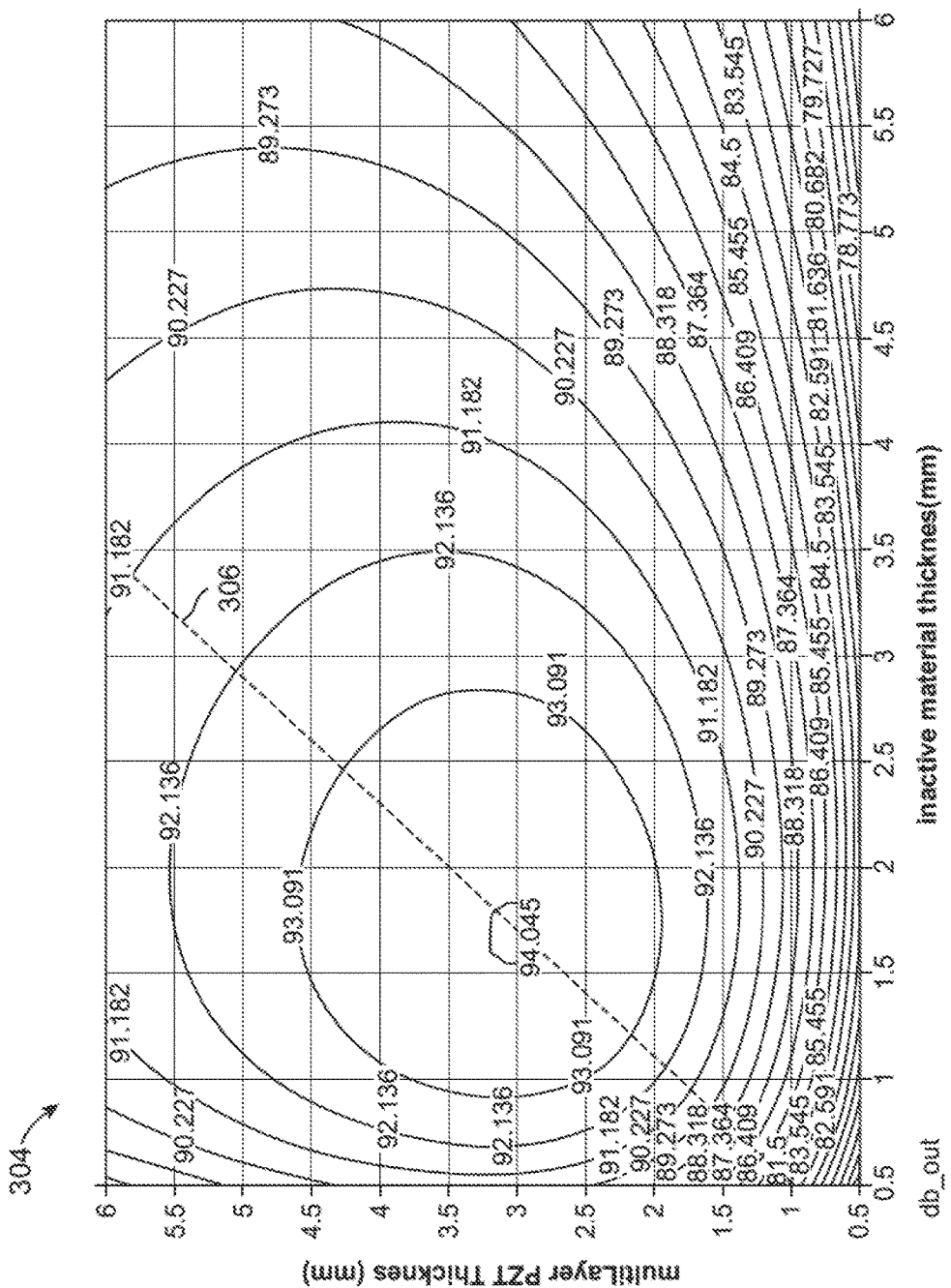
Figure 38:
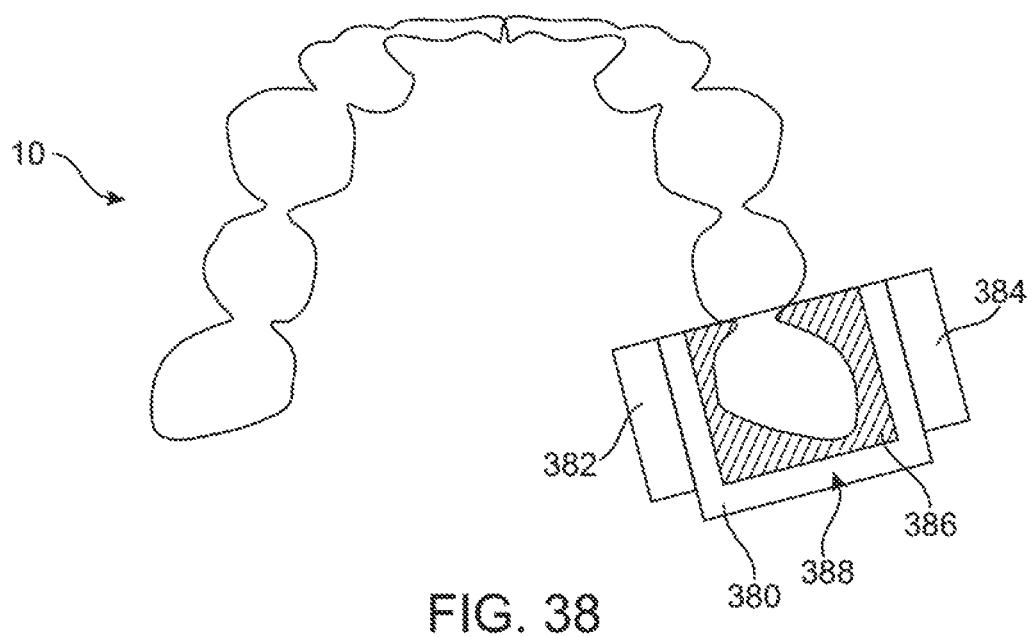
FIG. 38 shows a top view of another variation of one or more actuators positioned along a housing which is configured to be placed around a posterior surface of a tooth.

FIGS. 23A and 23B show plots 300 and 304, respectively, which also illustrate the relationship of dB output as a function of housing thickness and piezoelectric transducer material thickness for a particular variation of the housing having a span member configured for placement along a posterior surface of a tooth, as shown in FIG. 38. For these particular examples, line 302 in plot 300 and line 306 in plot 304 both represent optimal output values for a given device size where a thickness of the span in FIG. 23A is 2.25 mm and a thickness of the span in FIG. 23B is 7.5 mm. These illustrations are intended merely as examples of the relational correlation between the various parameters and the relative outputs for given span thicknesses. Moreover, these values are not intended to be limiting in any manner and are merely exemplary.

Figure 24:
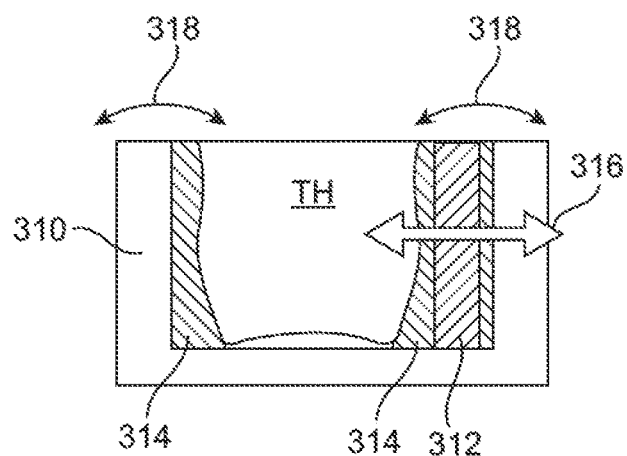
FIG. 24 shows a cross-sectional representation of an actuator positioned along a buccal or lingual tooth surface within the housing for effecting actuation of both sides of the tooth through the use of a single actuator.

Turning now to placement of the transducer assembly relative to the tooth or teeth TH and also with respect to the housing, any number of configurations is available for use. For example, FIG. 24 shows one example of a piezoelectric transducer 312 positioned within a housing 310 for direct placement against the tooth or teeth TH. Housing 310 may have a thickness of, e.g., 0.4 mm with a span member having a length, e.g., of 10 mm. The housing 310 may have a length of 7 mm for placement along one or more teeth TH. Furthermore, the piezoelectric transducer 312 may have a height of 7 to 9 mm. Of course, these values are given as examples and are subject to change depending variables such as the desired vibrational conductance as well as variables in a user's particular dentition, among other factors.

Generally, the housing 310 may be comprised of a single continuous mechanical member configured to have portions of itself face opposite sides of the tooth or teeth TH. The actuator assembly may be effectively pressed against the tooth TH utilizing the housing as a foundation and the housing 310 itself may be symmetric or non-uniform in its configuration. In one example, the arm portions of the housing may be placed along opposing surfaces of at least one tooth, e.g., along the respective lingual and buccal surfaces of the tooth or teeth. The arm portions may be coupled to one another via the span member such that the arms are urged or otherwise biased towards one another such that they press against their respective tooth surfaces. A housing with a relatively soft material may utilize a configuration and stiffness where a first resonant frequency mode of the span portion is below a region of interest while a first resonant frequency mode of the arm portion is within, near the upper range, or above the upper end of the frequency range of interest, as described above. As the transducer is driven past the first mode of the span portion, the span may appear to become relatively stiffer, thereby increase the force output of the system. Alternatively, additional mass can be added provided that the mass is added in such a way to ensure that the resonance of the arm member remains at the upper end of the frequency range of interest.

Figure 25:
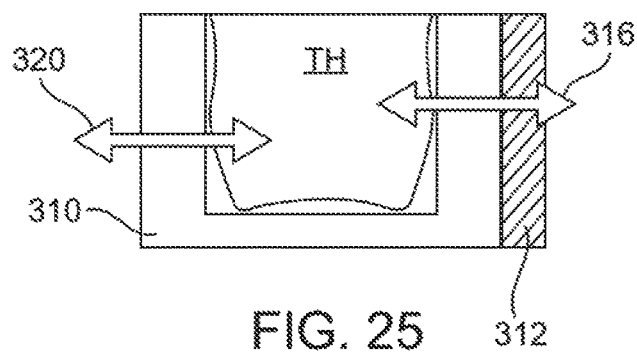
FIG. 25 shows a cross-sectional representation of an actuator positioned outside the housing for effecting two-point actuation.

With transducer 312 positioned within housing 310, a coupling impedance matching material 314, such as silicone, may be placed between piezoelectric transducer 312 and the surface of tooth TH to optimize conductance of vibrations 316 to the tooth TH. In this particular design, the arm members of housing 310 may be both driven 318 to flex relative to the tooth TH and may facilitate transmission of vibrations. FIG. 25 shows another variation also utilizing a single piezoelectric transducer 312 positioned along an outer surface of the housing 310. In this example, the piezoelectric element 312 drives the housing 310 in a unimorph-like manner pushing against the housing 310 and squeezing the tooth TH from both sides. The vibratory motion of transducer 312 may be transmitted 316, 320 by both arm members into opposing surfaces of tooth TH rather than directly against a single surface of the tooth TH.

Figure 26:
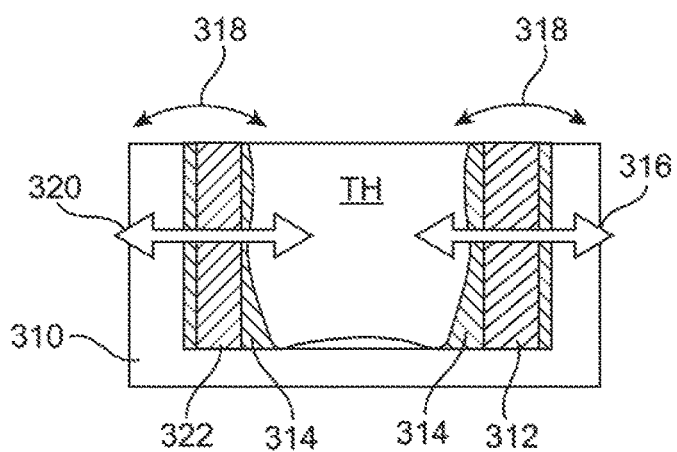
FIG. 26 shows a cross-sectional representation of two actuators positioned along both surfaces of a tooth or teeth within the housing for effecting two-point actuation.

FIG. 26 shows another variation utilizing two-point actuation where at least two transducers 312, 322 may both be positioned within housing 310 directly against opposite surfaces of tooth TH. In this variation, first transducer 312 may vibrate 316 along a first surface of tooth TH and second transducer 322 may vibrate 320 along a second surface of tooth TH. Moreover, both transducers 312, 322 may be configured to vibrate simultaneously or out-of-phase, depending upon the desired results.

Figure 27:
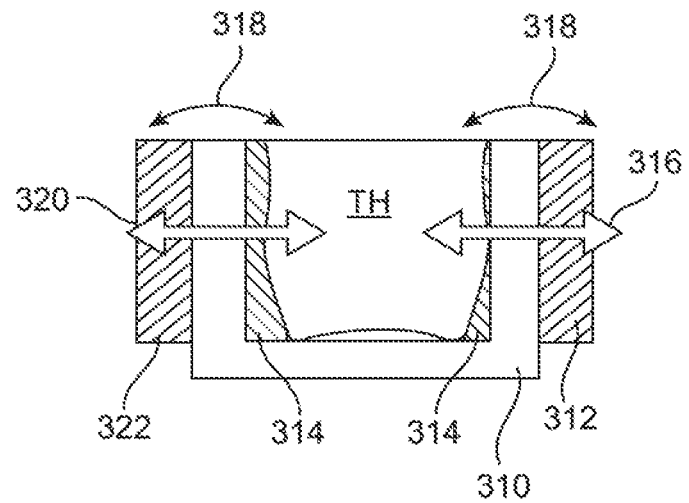
FIG. 27 shows a cross-sectional representation of two actuators positioned outside opposite surfaces of the housing for effecting symmetric bender actuation.
Figure 28:
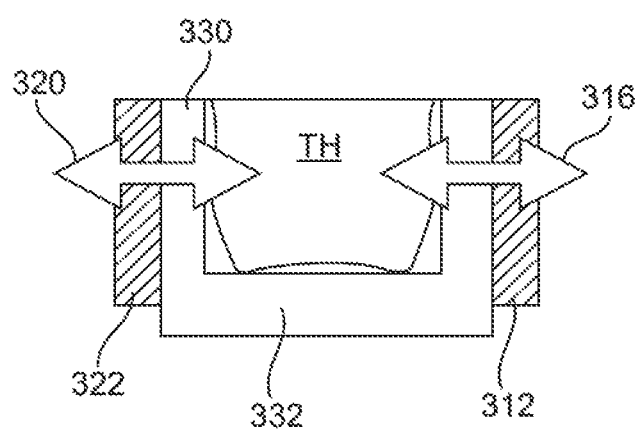
FIG. 28 shows a variation similar to the variation of FIG. 27 but with a housing having a span which is thicker relative to the span of FIG. 27.

FIG. 27 shows another variation utilizing two-point actuation where at least two transducers 312, 322 are positioned along outer surfaces of housing assembly 310. In this example, the respective vibrations 316, 320 may be transmitted through the housing 310, through coupling material 314, and into tooth TH. FIG. 28 shows an example similar to the variation in FIG. 27 where transducers 312, 322 may be mounted along an outer surface of housing 330 on opposite sides of tooth TH, but span member 332 connecting both arm members of housing 330 is thicker, e.g., twice as thick as the span member of housing 310 of FIG. 27. The increased thickness of span member 332 may result in a relatively stiffer span member 332 which increases an amplitude of the transmitted vibrations 316, 320.

Figure 29:
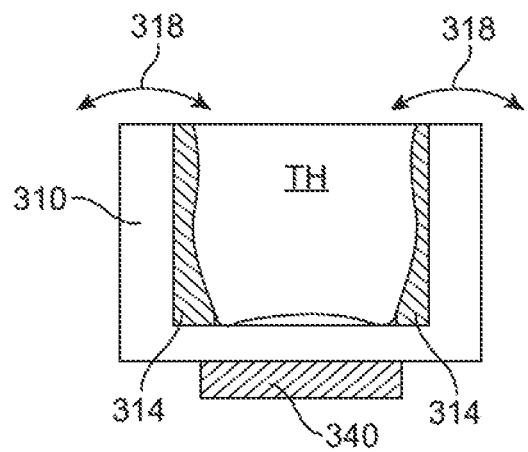
FIG. 29 shows a cross-sectional representation of an actuator mounted directly along a span portion of the housing.
Figure 30:
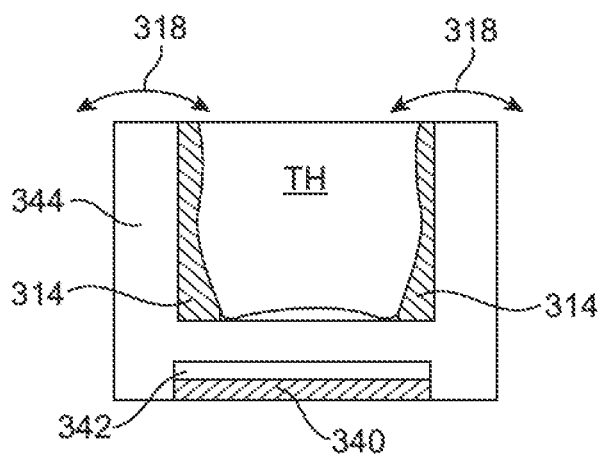
FIG. 30 shows a cross-sectional representation of an actuator mounted adjacent to the span portion of the housing.
Figure 31:
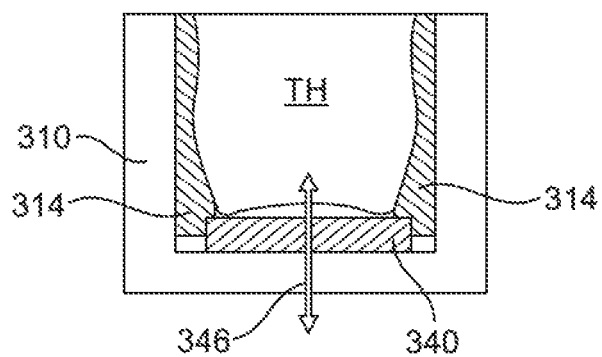
FIG. 31 shows a cross-sectional representation of an actuator mounted along the span portion within the housing directly in contact against an occlusal surface of the tooth or teeth.

Other symmetric bender actuation configurations are illustrated, for example, in FIG. 29 which shows transducer 340 positioned along an outer surface of the span portion of housing 310. Actuation of transducer 340 may not only oscillate the arm members of the housing 310, but may transmit the vibrations through an occlusal surface of tooth TH. FIG. 30 illustrates a similar variation where transducer 340 is positioned along the span portion of housing 344 separated by a gap 342 between transducer 340 and the remainder of housing 344. And FIG. 31 illustrates yet another variation where transducer 340 is positioned within housing 310 for placement directly against the occlusal surface of tooth TH such that vibrations 346 from transducer 340 are transmitted directly into the tooth TH.

Figure 32:
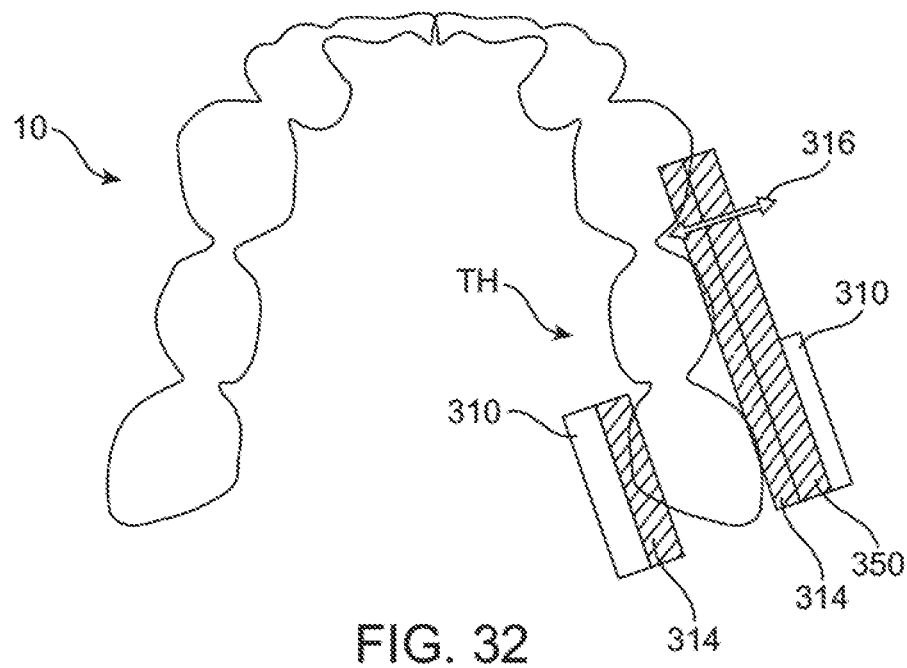
FIG. 32 illustrates a top view of an actuator mounted along the buccal surfaces of multiple teeth.

Some of the various configurations for actuator placement relative to the tooth and/or housing have been illustrated. Additional variations for positioning the housing and vibrational mechanisms over multiple teeth are now illustrated. Turning now to FIG. 32, a top view of actuator 350 is shown mounted along the buccal surfaces of multiple teeth TH. The transducer 350 may be mounted between an arm member of housing 310 and the surface of teeth TH with the coupling material 314 placed therebetween. Although housing 310 may extend along the length of a single tooth, transducer 350 may extend along several teeth.

Figure 33:
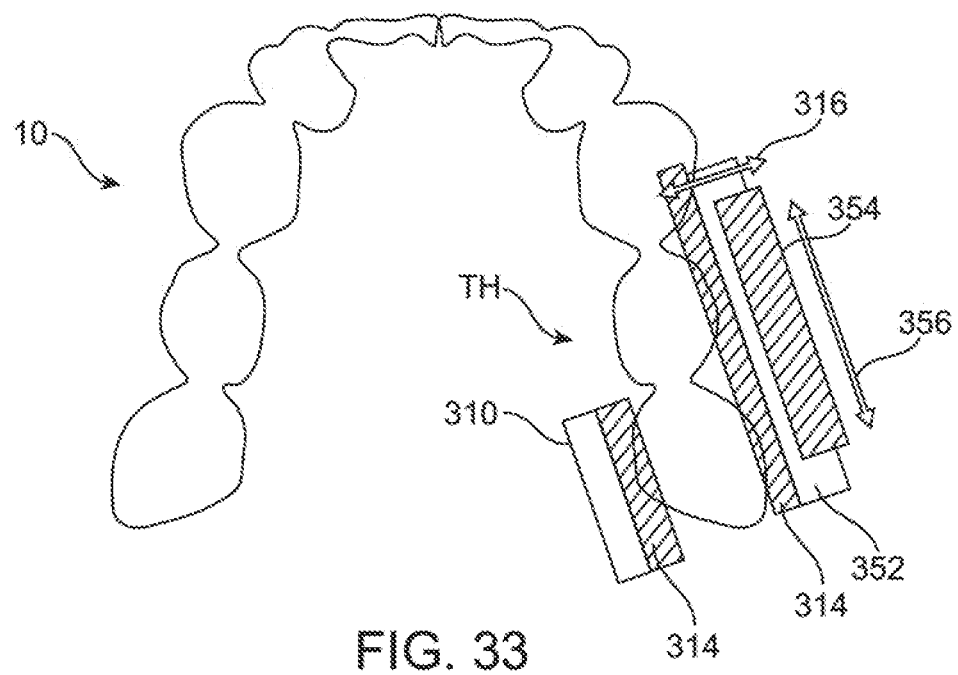
FIG. 33 illustrates a top view of another variation of an actuator which is configured to oscillate in the elongational direction to cause bending along an arm portion of the housing.

FIG. 33 shows another variation where transducer 354 may be placed along an outer surface of an arm member 352 of housing 310 and having an arm member which extends over several teeth. Transducer 354 may be configured to vibrate along a longitudinal direction 345 such that the transducer pushes and pulls causing bending 316 in the elongate arm member 352 and pushing on the teeth TH.

Figure 34A:
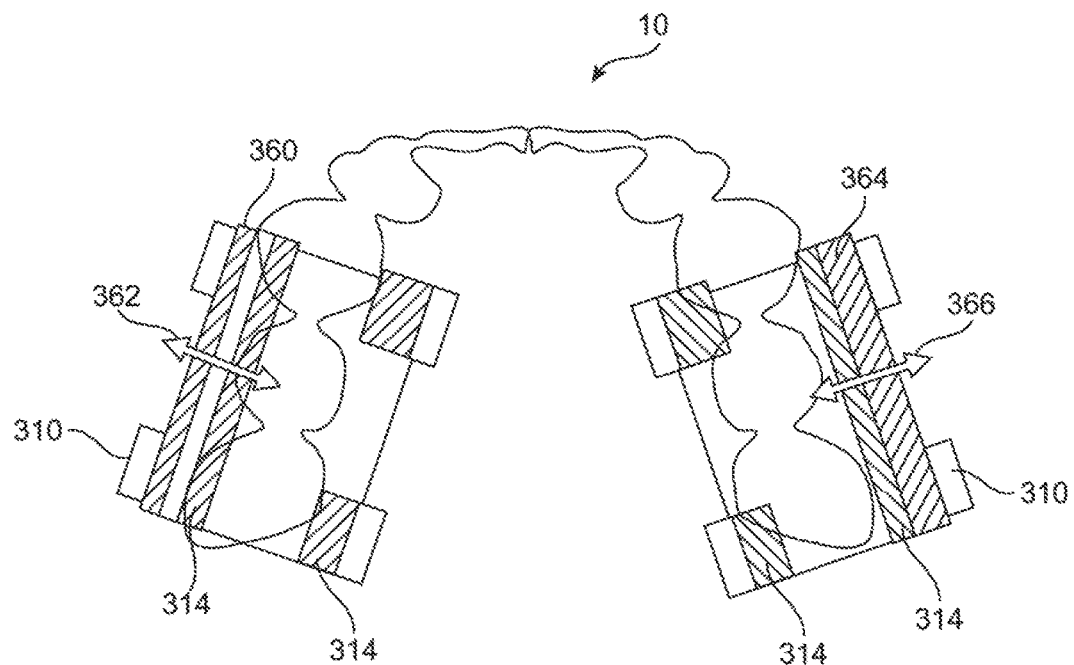
FIG. 34A illustrates a top view of another variation of multiple actuators positioned over multiple teeth.
Figure 34B:
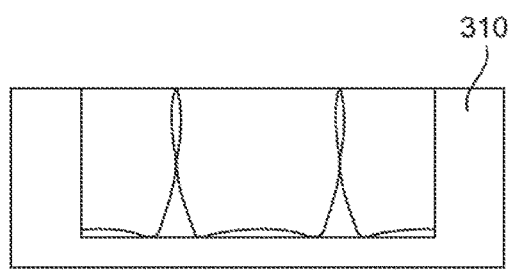
FIGS. 34B and 34C show side and end views, respectively, of another variation for the housing configuration.
Figure 34C:
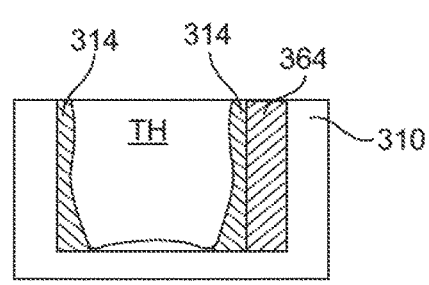

FIG. 34A shows yet another example where at least two housing assemblies may be utilized on both sides of a patient's dentition 10. The first housing may utilize a transducer 360 positioned along the housing and vibrating 362 against the teeth and the second housing may similarly utilize a transducer 364 also vibrating 366 against the teeth. FIG. 34B shows a side view of an example of the housing 310 along a lingual surface of the teeth TH where a portion of the teeth are utilized for securing the housing. FIG. 34C shows a partial cross-sectional side view illustrating the transducer 364 secured within the housing 310 for direct placement against the teeth TH. Any of the various transducer and housing configurations shown herein may be utilized in either the first and/or second housing configurations.

Figure 35:
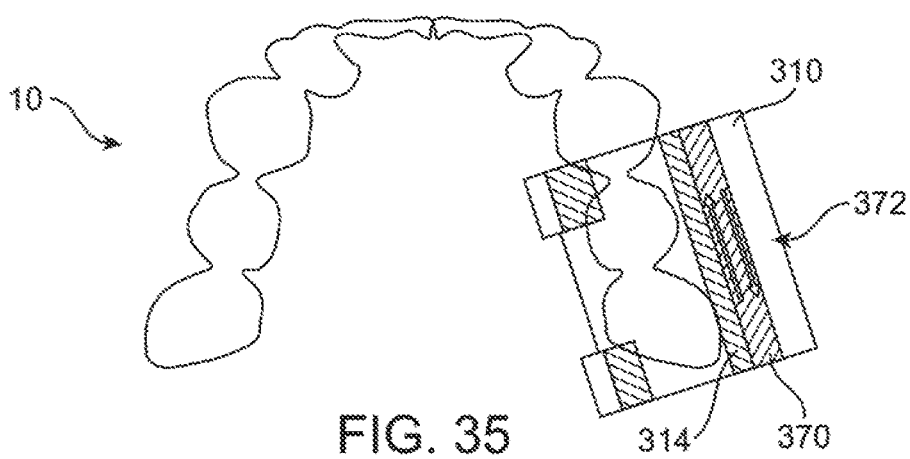
FIG. 35 shows a top view of another variation of an actuator positioned along multiple teeth which utilizes a shearing oscillation.
Figure 36:
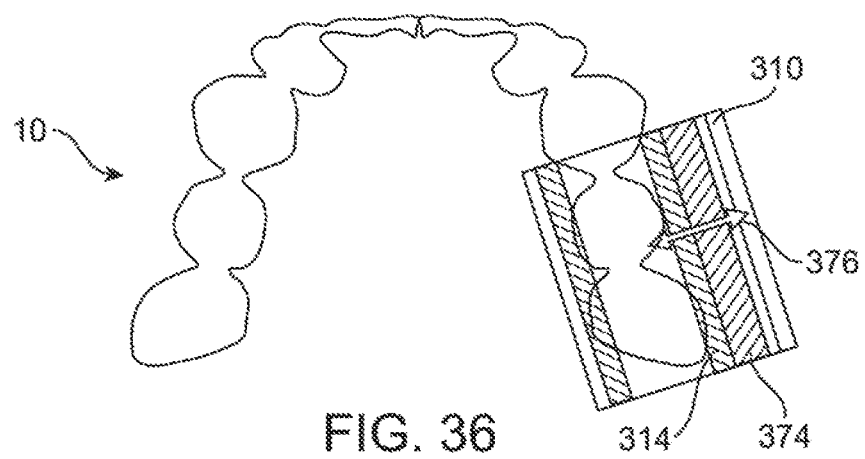
FIG. 36 shows a top view of another variation of an actuator positioned against multiple teeth.
Figure 37:
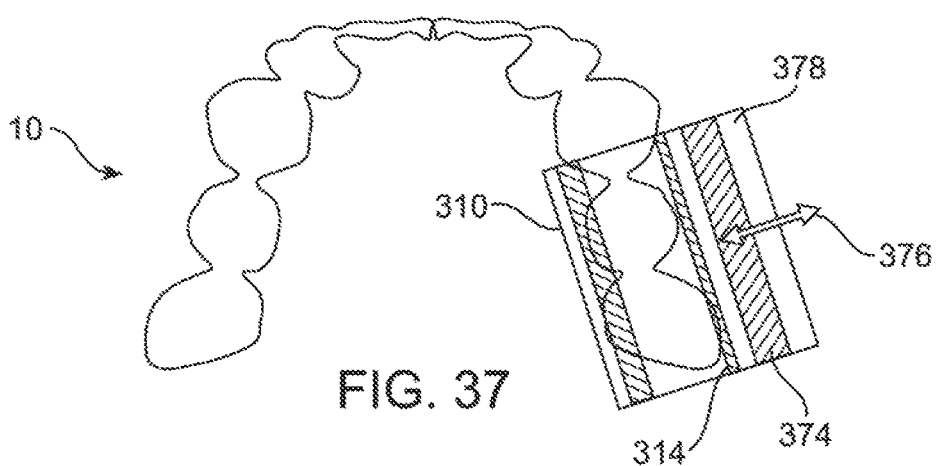
FIG. 37 shows a top view of another variation of an actuator positioned along multiple teeth within the housing.

FIG. 35 shows yet another variation of an assembly utilizing a transducer 370 configured to vibrate in a shear mode where opposing surfaces of the transducer 370 vibrate in opposing directions 372. The shearing motion 372 is applied to the teeth through the impedance matching layer 314 and directly generates forces in the tooth. FIG. 36 shows another variation where transducer 374 is configured to vibrate in a transverse direction 376 while contained within a housing 310 which is stiffened. Because housing 310 is relatively stiffer than other configurations, housing 310 is less prone to bending and flexing such that the vibrations 376 may be transferred into each underlying tooth contacted by coupling material 314 and transducer 374. FIG. 37 also shows another configuration utilizing transducer 374 having an additional mass 378 which may be accelerated by transducer 374 to generate a force sufficient for conducting into the underlying teeth.

Another alternative configuration is shown in FIG. 38, which illustrates a housing 380 having a span member 388 which is positioned around and in contact against a posterior surface of a tooth. One or more transducer assemblies 382, 384 may be positioned along the arm members of housing 380 for oscillating either against an outer surface of housing 380, as shown, or for direct placement against the lingual and buccal surfaces of the tooth. Coupling material 386 may be placed between housing 380 and the underlying tooth to facilitate transmission of vibrations and ease of insertion of the oral appliance. Examples of design parameters for this particular configuration of housing 380 are shown in FIGS. 23A and 23B, as described above.

Figure 39:
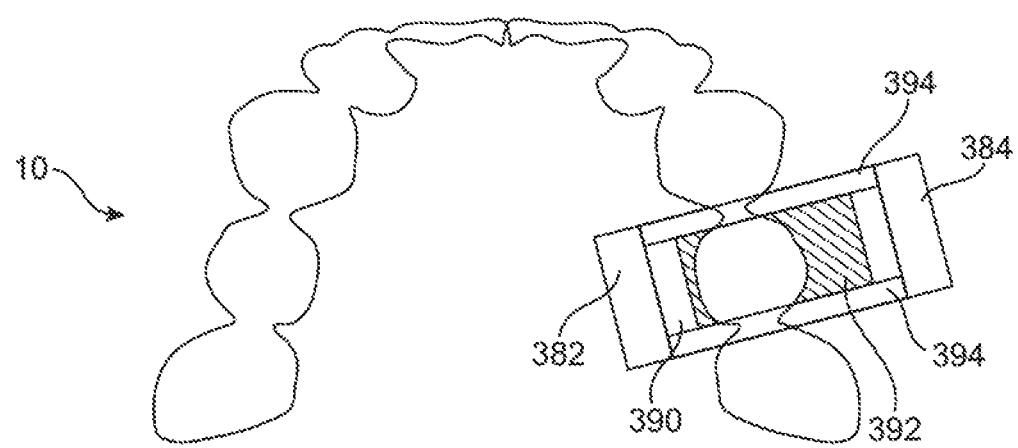
FIG. 39 shows a top view of another variation of one or more actuators which are positioned along both buccal and lingual surfaces and which are connected to one another via wires or members which are positioned below the occlusal surfaces.

FIG. 39 shows yet another variation where the arm portions of housing 390 may be placed along both lingual and buccal surfaces of a tooth while connected to one another via span members which are configured as wires 394. The wires 394 may be routed such that they are positioned below the occlusal surfaces of the teeth or between the teeth so as to be minimally obtrusive. Moreover, transducer assemblies 382, 384 may be positioned along the outer surfaces of housing 390, as shown, or they may be placed directly against the tooth surfaces. In either case, a coupling material 392 may be placed against the tooth to facilitate transmission of vibrations therethrough.

FIGS. 40A and 40B show top and cross-sectional views, respectively, of a housing assembly 400 having a mass 404 attached to an arm member 408 which extends from the span 406 of the housing 400. The piezoelectric transducer 402, which is attached to member 403 thereby becoming an actuator, acts, in concert with member 403 as a unimorph to push directly on the underlying tooth or teeth TH. The actuator is attached to the housing 400 at its two ends points. This arrangement of attachment allows the actuator to actuate with necessitating motion of the housing 400 and mass 404. The system is such that the mass 404 and housing 400 resonance is relatively low. Hence, while very pliable and soft on a human scale, it may provide a sufficiently solid foundation in the frequency range of interest to allow the unimorph to generate large forces on the tooth TH during actuation. While a unimorph is depicted, a cap device or any of the other transducer architectures described herein may be used in place of the unimorph transducer. FIG. 41 shows another variation which also utilizes additional mass elements 410, 412 which are attached to an outer surface of housing 400 adjacent to transducer 402 rather than along a separately movable arm member 408. Although shown with two mass elements 410, 412, additional masses may be utilized depending upon the desired transmission results.

Figure 42A:
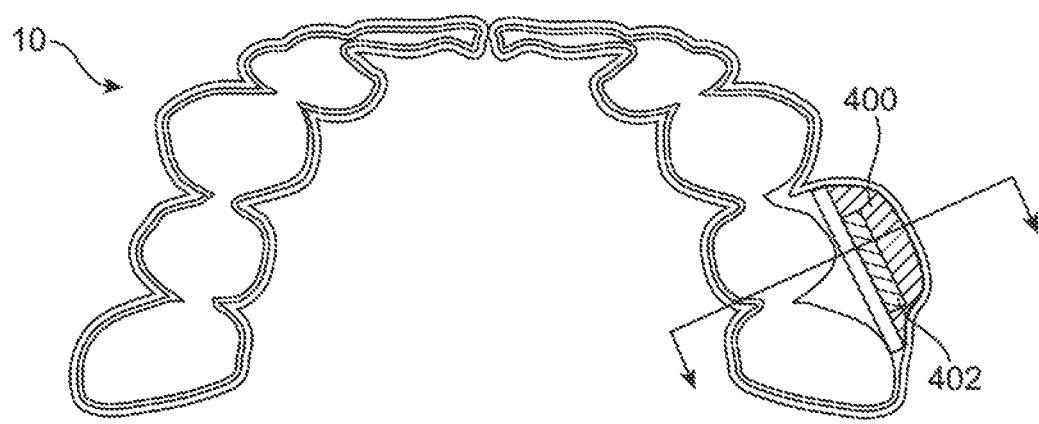
FIGS. 42A and 42B show top and cross-sectional side views of another variation of an actuator having a low impedance reflective layer adjacent to the transducer.
Figure 42B:
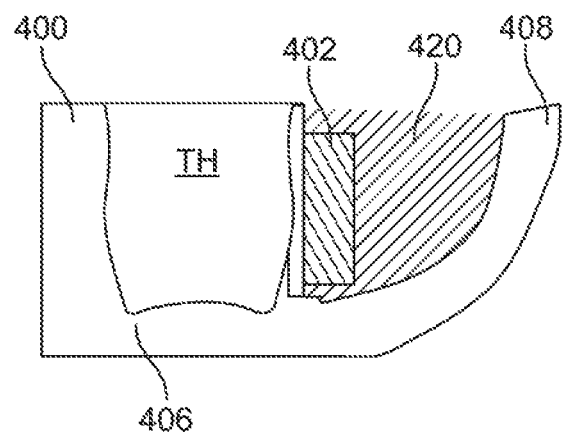

FIGS. 42A and 42B show top and cross-sectional views, respectively, of yet another variation utilizing a housing 400 and piezoelectric transducer 402 coupled directly to a tooth surface. In this variation, arm member 408 extends separately from span member 406, as above, but also includes a low impedance reflective layer 420 surrounding transducer 402 and also between transducer 402 and arm member 408. The reflective layer 420 may be comprised of a material, such as silicone, which acts to reflect vibrational energy transmitted from transducer 402 and retransmit the energy back into tooth TH.

Figure 43A:
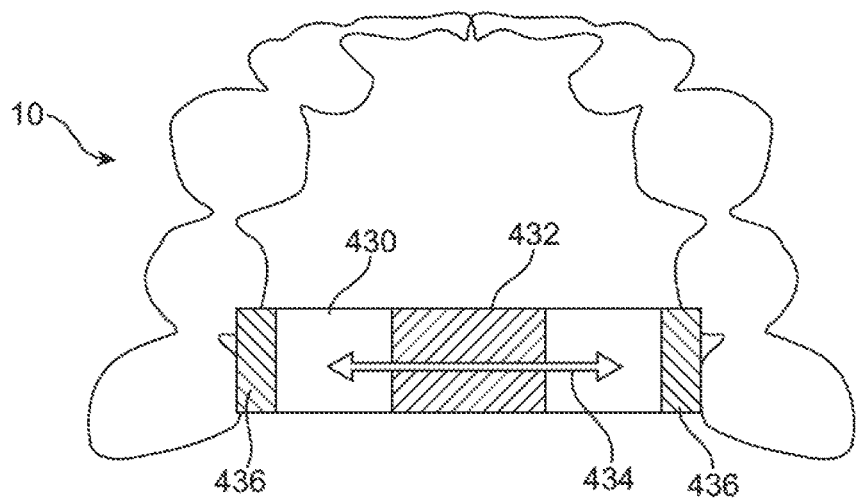
FIGS. 43A and 43B show top and side views of another variation of the actuator configured to be retained against a user's palatal surface while transmitting vibrations through the tooth or teeth.
Figure 43B:
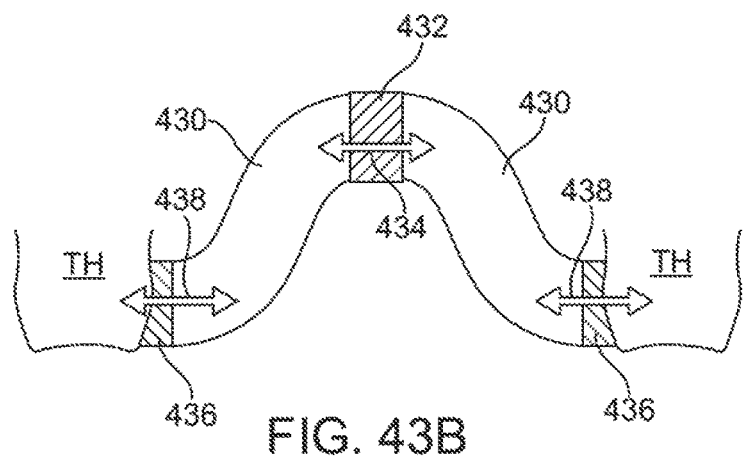
Figure 43C:
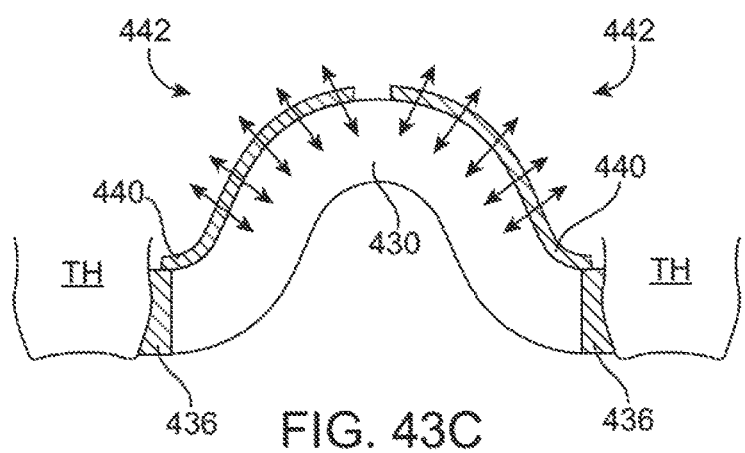
FIG. 43C shows a side view of another variation of a palatal configuration in which the transducer(s) transmits vibrations through the palatal surface.

Aside from transducer and housing assemblies which are positioned along or against one or more teeth, transducer assemblies may be alternatively mounted along a retainer-like structure configured for placement adjacent or along the palate of the user. Similar to other variations described above, arch 430 may extend between coupling portions 436 which are configured to extend from the arch 430 for placement against the lingual surfaces of teeth TH on opposite sides of the user's dentition, as illustrated in FIG. 43A. Rather than utilizing transducer assemblies directly upon the teeth, transducer 432 may be removably or permanently integrated along arch 430 such that elongational vibration 434 of the transducer 432 conducts the vibrations along arch 430 for transmission 438 through coupling portions 436 and into the user's teeth TH, as shown in the partial cross-sectional side view of FIG. 43B. Alternatively, one or more transducers 440 may be positioned along arch 430 and actuated to directly conduct vibrations 442 through the user's palatal bone, as shown in FIG. 43C. A layer of polyvinylidene fluoride (PVDF), for example, may generate the desired vibrations.

Figure 44:
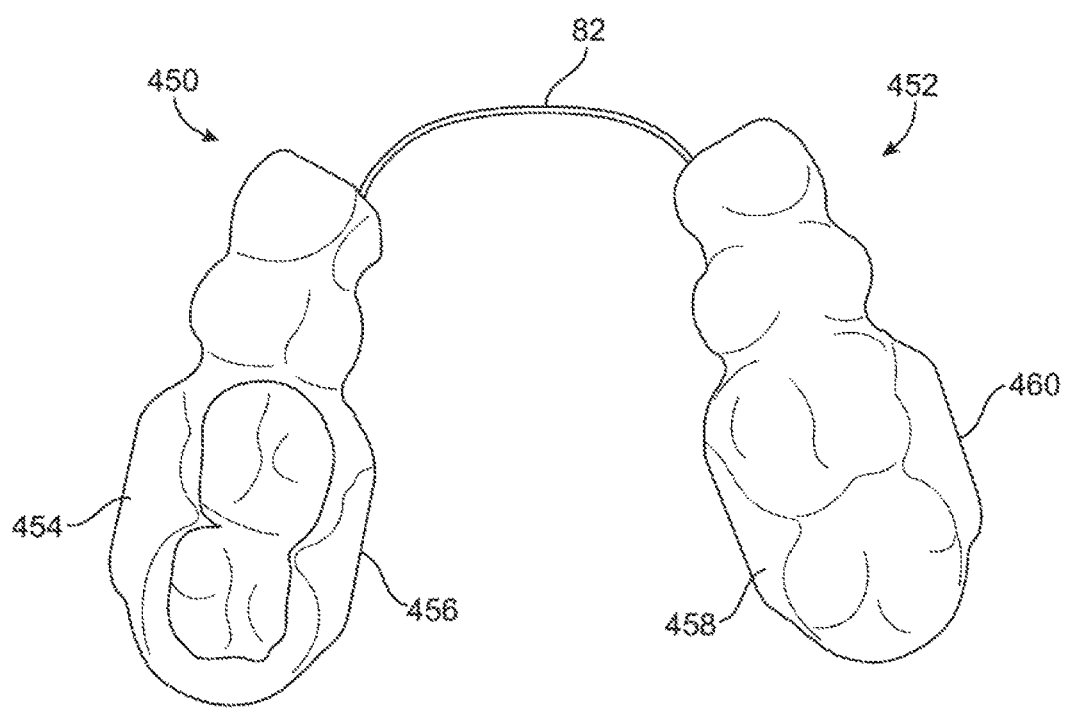
FIG. 44 shows a top view of yet another variation where one or more actuators may be attached to a retainer.

FIG. 44 shows yet another variation similar to the configuration shown above in FIG. 8A which utilizes connecting member 82 which may be positioned along the lingual or buccal surfaces of a patient's row of teeth to connect a first tooth retaining portion 450 and a second tooth retaining portion 452. One or more transducer assemblies 454, 456 may be integrated within the first retaining portion 450 to align along the buccal and lingual surfaces of one or more teeth. Similarly, one or more transducer assemblies 458, 460 may also be integrated within the second retaining portion 452 to align along the lingual and buccal surfaces of one or more teeth. Such a configuration may be particularly useful in incorporating a number of transducers positioned at various locations along the dentition, as described in further detail in U.S. patent application Ser. No. 11/672,239, which has been incorporated by reference above.

The applications of the devices and methods discussed above are not limited to the treatment of hearing loss but may include any number of further treatment applications. Moreover, such devices and methods may be applied to other treatment sites within the body. Modification of the above-described assemblies and methods for carrying out the invention, combinations between different variations as practicable, and variations of aspects of the invention that are obvious to those of skill in the art are intended to be within the scope of the claims.

What is claimed is:

1. An apparatus, comprising:
a housing that is configured to engage at least one tooth without requiring anatomical modification of the at least one tooth or bonding to the at least one tooth;
a transducer disposed within or upon the housing and configured to transmit vibrations to a surface of the at least one tooth, wherein said apparatus produces an interference fit between the apparatus and at least two surfaces of the at least one tooth;
an electronics assembly in communication with the transducer; and
a mass element coupled to the transducer and movable relative to the housing whereby movement of the mass element generates a force transmittable through the surface of the at least one tooth.

2. The apparatus of claim 1 wherein the housing comprises at least two arm members configured to be placed against opposite sides of the at least one tooth in a secure manner and a span member joining the two arm members.

3. The apparatus of claim 2 wherein the housing is removably securable to the at least one tooth.

4. The apparatus of claim 2 wherein the span member is configured to be placed against a posterior surface of the at least one tooth.

5. The apparatus of claim 1 wherein the housing comprises at least a first arm member configured to be placed against a first side of the at least one tooth and at least a second arm member configured to be placed against a second side of the tooth, and a span member that joins the first and second arm members.

6. The apparatus of claim 1 wherein the housing comprises an oral appliance that conforms to the at least one tooth.

7. The apparatus of claim 1 wherein the electronic assembly is disposed within or upon the housing.

8. The apparatus of claim 7 wherein the electronic assembly is encapsulated within the housing.

9. The apparatus of claim 7 wherein the electronic assembly further comprises a power supply in electrical communication with the transducer.

10. The apparatus of claim 9 wherein the power supply comprises a battery.

11. The apparatus of claim 9 wherein the power supply is rechargeable.

12. The apparatus of claim 8 wherein the electronic assembly further comprises a processor in electrical communication with the transducer.

13. The apparatus of claim 12 further comprising a microphone in electrical communication with the processor.

14. The apparatus of claim 8 wherein the electronic assembly further comprises a receiver in wireless communication with an externally located transmitter assembly.

15. The apparatus of claim 1 wherein the transducer is disposed along an outer surface of the housing.

16. The apparatus of claim 1 wherein the transducer is disposed along an inner surface of the housing against the surface of the at least one tooth.

17. The apparatus of claim 1 further comprising at least one additional transducer disposed within or upon the housing and configured to be in vibratory communication with a second surface of the at least one tooth or at least a second tooth.

18. The apparatus of claim 1 wherein the transducer is configured to be in vibratory communication with a buccal surface of the at least one tooth.

19. The apparatus of claim 1 wherein the transducer comprises an electromagnetic transducer having the mass element freely movable relative to the transducer.

20. The apparatus of claim 1 wherein the transducer comprises a piezoelectric transducer configured to vibrate in a direction transverse to a length of the transducer.

21. The apparatus of claim 1 wherein the transducer comprises a piezoelectric transducer configured to vibrate in an elongate direction relative to the transducer.

22. The apparatus of claim 1 wherein the transducer comprises a piezoelectric transducer configured to vibrate in a shear mode such that opposing surfaces of the transducer vibrate in opposing directions.

23. The apparatus of claim 1 wherein the transducer comprises a unimorph or bimorph composite transducer configured to vibrate in a bending mode.

24. The apparatus of claim 1 wherein the transducer is coupled to the mass element at a center of the transducer and wherein the transducer is further coupled to the housing around a circumference of the transducer.

25. The apparatus of claim 1 wherein the force transmitted through the surface of the at least one tooth is constant over a frequency range of interest.

26. The apparatus of claim 1 wherein the apparatus is configured to be removable from the at least one tooth.

27. The apparatus of claim 1 wherein the housing comprises a polymeric material.

* * * * *